(12) United States Patent  (10) Patent No.: US 7,758,493 B2
Gingras  (45) Date of Patent: Jul. 20, 2010

(54) GASTRIC CONSTRICTION DEVICE

(75) Inventor: Peter Gingras, Galway (IE)

(73) Assignee: Proxy Biomedical Limited, Galway (IE)

( * ) Notice: Subject to any disclaimer, the term of this patent is extended or adjusted under 35 U.S.C. 154(b) by 1551 days.

(21) Appl. No.: 10/972,044

(22) Filed: Oct. 22, 2004

(65) Prior Publication Data

US 2005/0119674 A1    Jun. 2, 2005

Related U.S. Application Data

(60) Provisional application No. 60/514,212, filed on Oct. 23, 2003.

(51) Int. Cl.
A61F 2/00 (2006.01)

(52) U.S. Cl. ...................................................... 600/37

(58) Field of Classification Search ............. 600/29–32, 600/37; 606/139, 151, 153, 154
See application file for complete search history.

(56) References Cited

U.S. PATENT DOCUMENTS

| | | |
|---|---|---|
| 3,875,928 A | 4/1975 | Angelchik |
| 4,052,988 A | 10/1977 | Doddi et al. |
| 4,271,828 A | 6/1981 | Angelchik |
| 4,403,604 A | 9/1983 | Wilkinson et al. |
| 4,458,681 A | 7/1984 | Hopkins |
| 4,592,339 A | 6/1986 | Kuzmak et al. |
| 4,696,288 A | 9/1987 | Kuzmak et al. |
| 4,747,849 A | 5/1988 | Galtier |
| 4,796,603 A | 1/1989 | Dahlke et al. |
| 4,803,985 A | 2/1989 | Hill |
| 4,854,316 A | 8/1989 | Davis |
| 5,074,868 A | 12/1991 | Kuzmak |
| 5,226,429 A | 7/1993 | Kuzmak |
| 5,246,456 A | 9/1993 | Wilkinson |
| 5,327,914 A | 7/1994 | Shlain |
| 5,345,949 A | 9/1994 | Shlain |
| 5,449,368 A | 9/1995 | Kuzmak |
| 5,549,621 A | 8/1996 | Bessler et al. |

(Continued)

OTHER PUBLICATIONS

Evolution of Operative Procedures for the Management of Morbid Obesity 1950-2000: Henry Buchward & Jane Buchwald—Obesity Surgery, 12, 705-717, 2002.

(Continued)

*Primary Examiner*—Charles A Marmor, II
*Assistant Examiner*—Christine D Hopkins
(74) *Attorney, Agent, or Firm*—Fish & Richardson P.C.

(57) ABSTRACT

A gastric constriction device (160) comprises a sheet (131) extending over part of the wall of the stomach (24). Five bands (151) extend around the stomach (24) to fix the sheet (131) in position relative to the stomach (24). The lower two bands (151) extend from the first side (152) of the sheet (131) around the stomach (24) only partially towards the second side (153). These lower two bands (151) are not fixed to the second side (153). This arrangement results in an unconstricted portion of the stomach (161). In this manner, the device (160) restricts expansion of the majority of the stomach wall while facilitating expansion of this unconstricted portion (161). The unconstricted portion (161) is therefore free to expand or bulge outwardly upon ingestion. This expansion may trigger the feeling of satiation due to the presence of the vagal nerves in this portion (161) of the stomach (24).

15 Claims, 27 Drawing Sheets

U.S. PATENT DOCUMENTS

| | | | |
|---|---|---|---|
| 5,601,604 | A | 2/1997 | Vincent |
| RE36,176 | E | 3/1999 | Kuzmak |
| 5,910,149 | A | 6/1999 | Kuzmak |
| 5,919,233 | A | 7/1999 | Knopf et al. |
| 5,938,669 | A | 8/1999 | Klaiber et al. |
| 6,511,490 | B2 | 1/2003 | Robert |
| 6,547,801 | B1 | 4/2003 | Dargent et al. |
| 6,558,400 | B2 | 5/2003 | Deem et al. |
| 6,564,094 | B2 | 5/2003 | Alferness et al. |
| 6,572,629 | B2 | 6/2003 | Kalloo et al. |
| 6,656,194 | B1 | 12/2003 | Gannoe et al. |
| 2002/0091395 | A1 | 7/2002 | Gabbay |
| 2002/0169464 | A1 | 11/2002 | Latour |
| 2002/0198548 | A1 | 12/2002 | Robert |
| 2003/0120288 | A1 | 6/2003 | Benchetrit |
| 2003/0158564 | A1 | 8/2003 | Benchetrit |
| 2004/0097989 | A1 | 5/2004 | Molina Trigueros |
| 2004/0107004 | A1 | 6/2004 | Levine et al. |
| 2004/0122293 | A1 | 6/2004 | Douglas et al. |
| 2004/0122456 | A1 | 6/2004 | Saadat et al. |
| 2004/0147942 | A1 | 7/2004 | Chao |
| 2004/0153106 | A1 | 8/2004 | Dudai |

OTHER PUBLICATIONS

Is There a Role for Gastric Accommodation and Satiety in Asymptomatic Obese People?: Doe-Young Kim, Michael Camilleri, Joseph A. Murray, Debra A. Stephens, James A. Levine, Duane D. Burton—Obesity Research, vol. 9, No. 11, Nov. 2001.

Independent Influences of Body Mass and Gastric Volumes On Satiation in Humans: Silvia Delgado-Aros, Filippo Cremonini, Janet E. Castillo, Heather J. Chial, Duane D. Burton, Irene Ferber, Michael Camilleri—Gastroenterology 2004: 126:432-440.

Implantable Gastric Stimulation for Weight Loss: Scott A. Shikora—Society for Surgery of the Allmentary Tract—2004.

Stomach Capacity in Obese Individuals: Allan Geliebter—Obesity Research, vol. 9, No. 11, Nov. 2001.

Development of a Test to Measure Gastric Accommodation in Humans: Sjoerd D. Kuiken, Melvin Samsom, Michael Camilleri, Brian P. Mullan, Duane D. Burton, Louis J. Kost, Timothy J. Hardman, Benjamin H. Brinkmann, Michael K. O'Connor—The American Physiological Society, 1999.

Late Complications After Gastric Reservoir Reduction With External Wrap: Steven A. Curley, William Weaver, Lawrence H. Wilkinson, Gerald B. Demarest—Arch Surg, vol. 122—Jul. 1987.

Gastric (Reservoir) Reduction for Morbid Obesity: Lawrence H. Wilkinson, Ole A. Peloso—Arch Surg, vol. 116—May 1981.

Gastrointestinal Surgery for Severe Obesity: National Institutes of Health Consensus Development Conference Statement. *Am J clin Nutr* 1992; 55: 615S-9S.

A Comparison of the Gastric Bypass and the Gastric Wrap for Morbid Obesity. Surg. Gynecol. Obstet. 1993; 176: 262-266.

Gastric Pacing as therapy for Morbid Obesity: Preliminary Results. Obesity Surgery 2002; 12: 12S-16S.

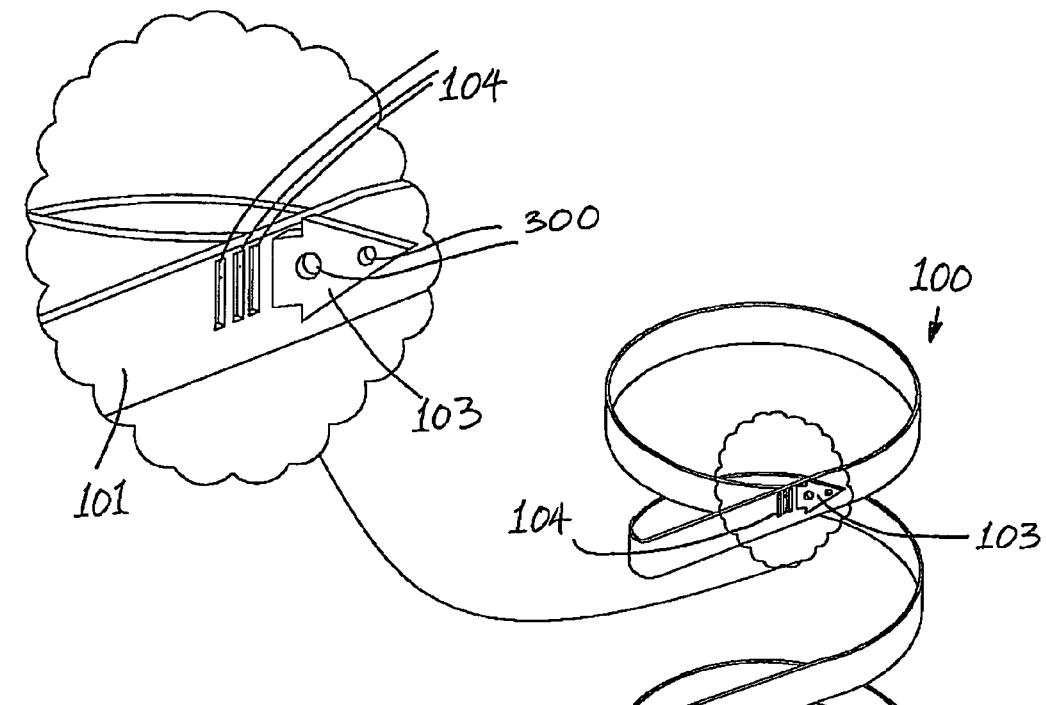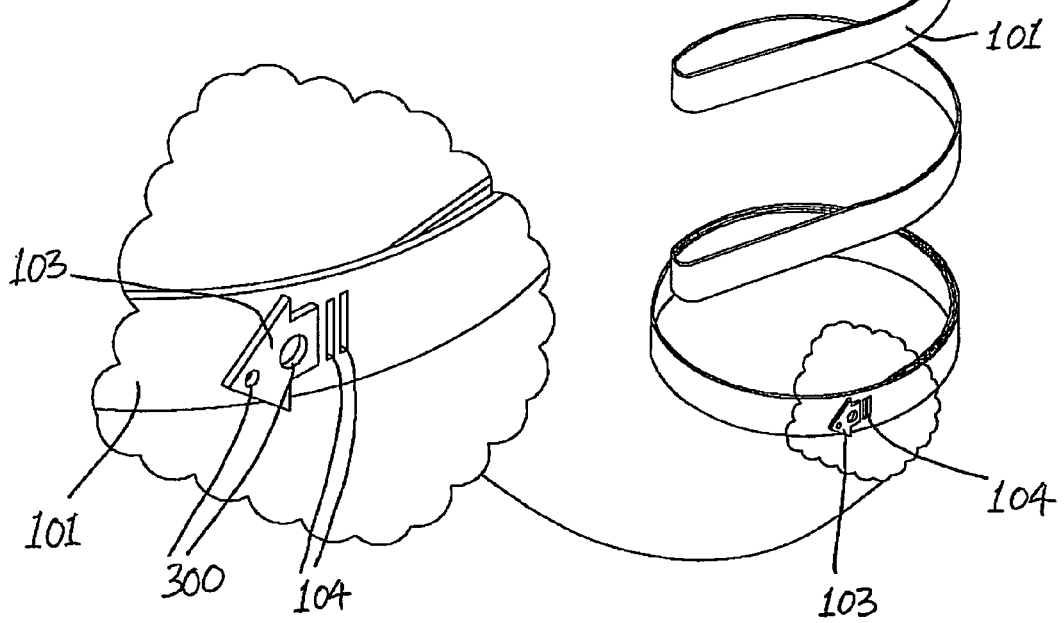
Fig. 2

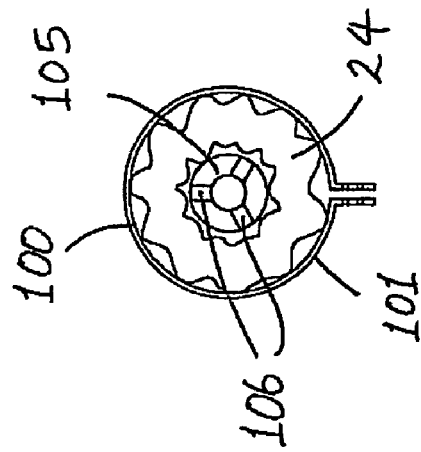
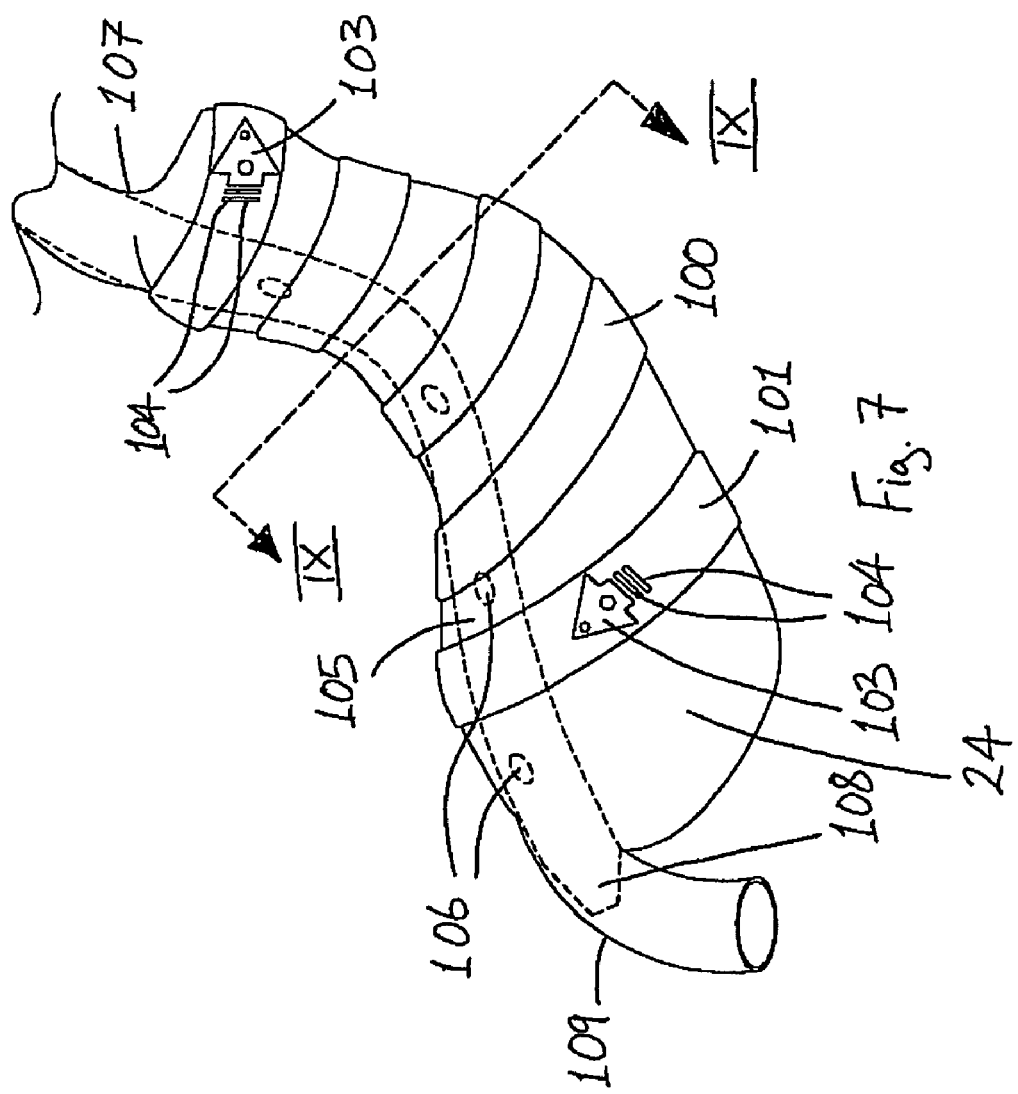
Fig. 9
Fig. 7

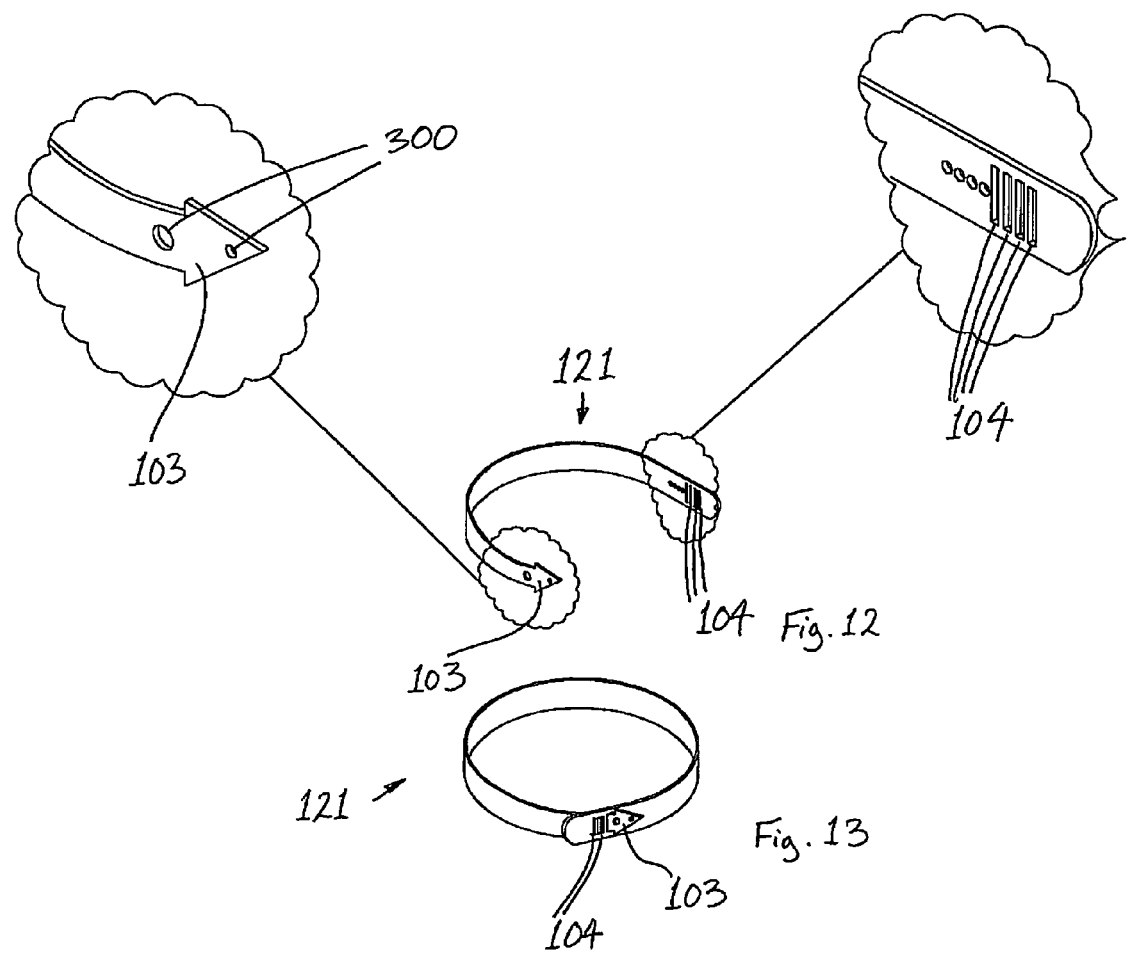

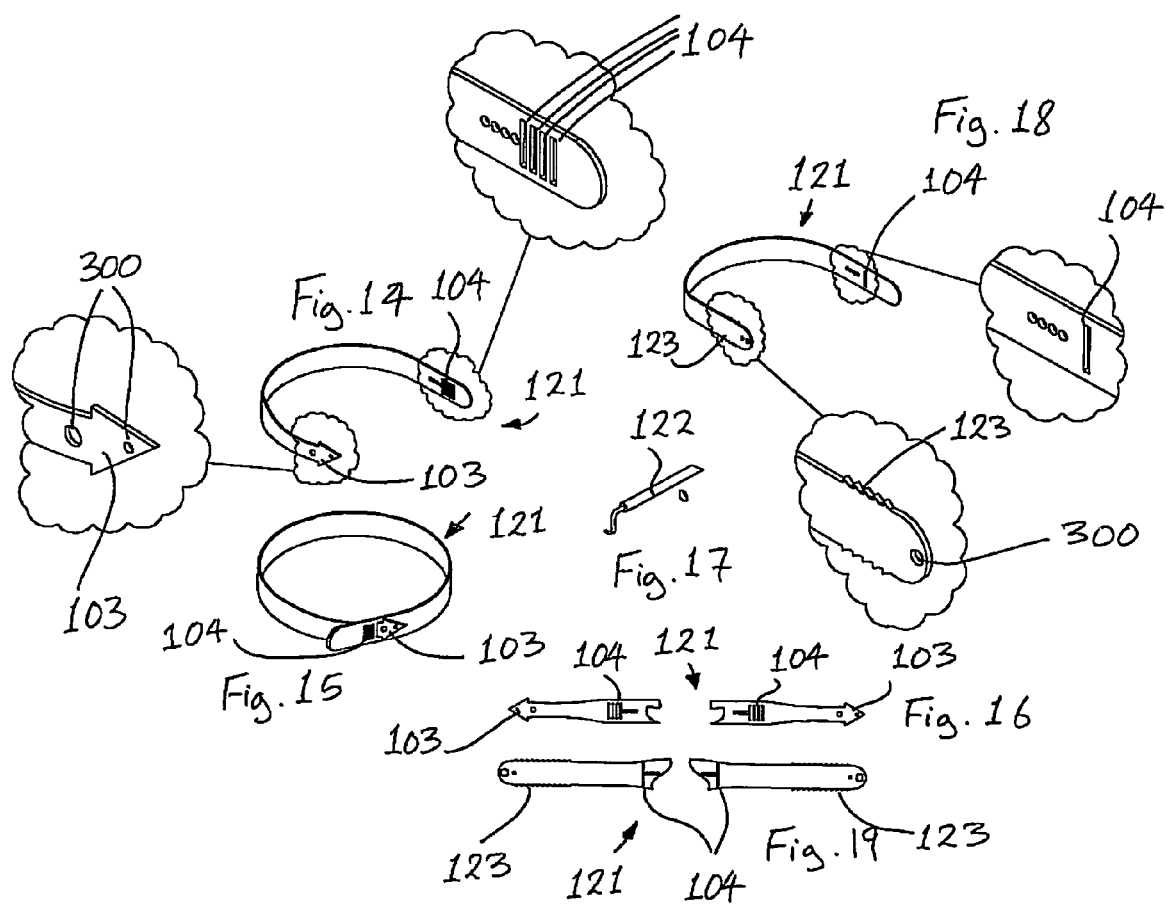

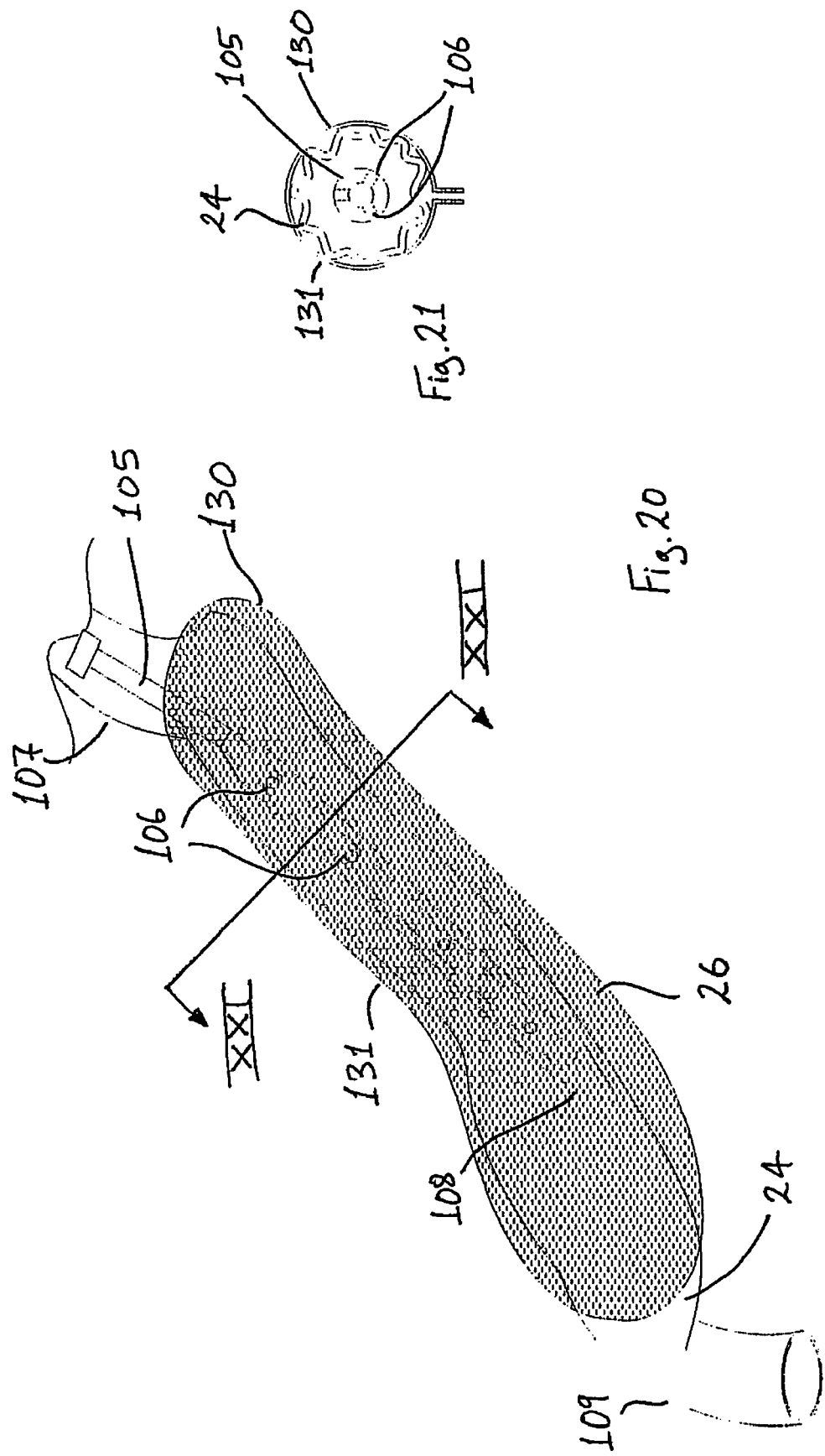

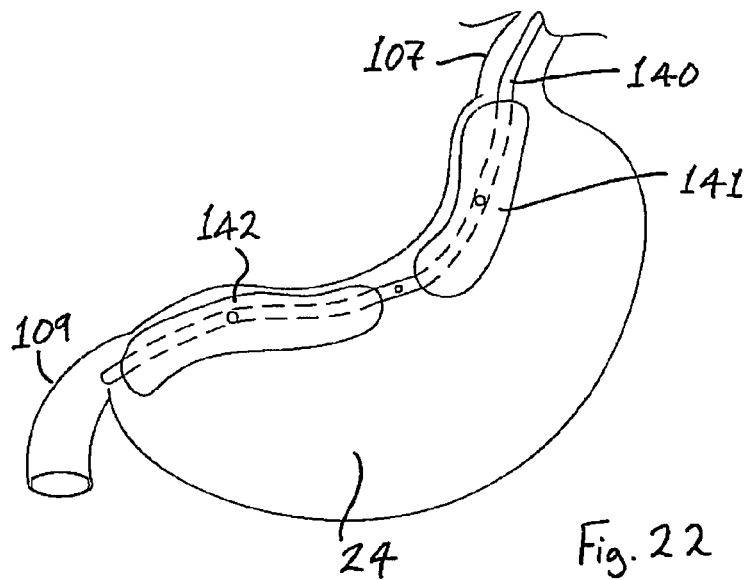
Fig. 22
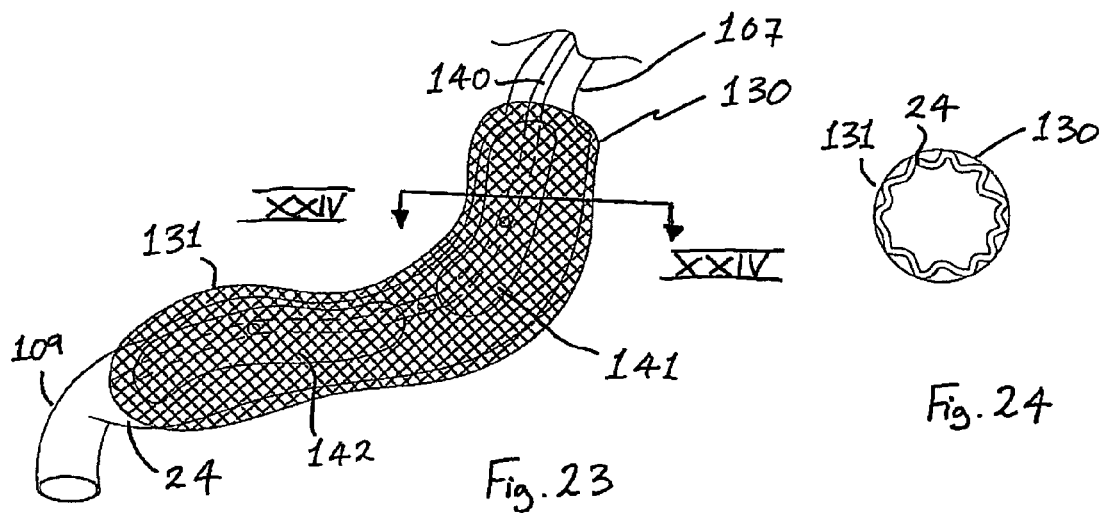
Fig. 23
Fig. 24

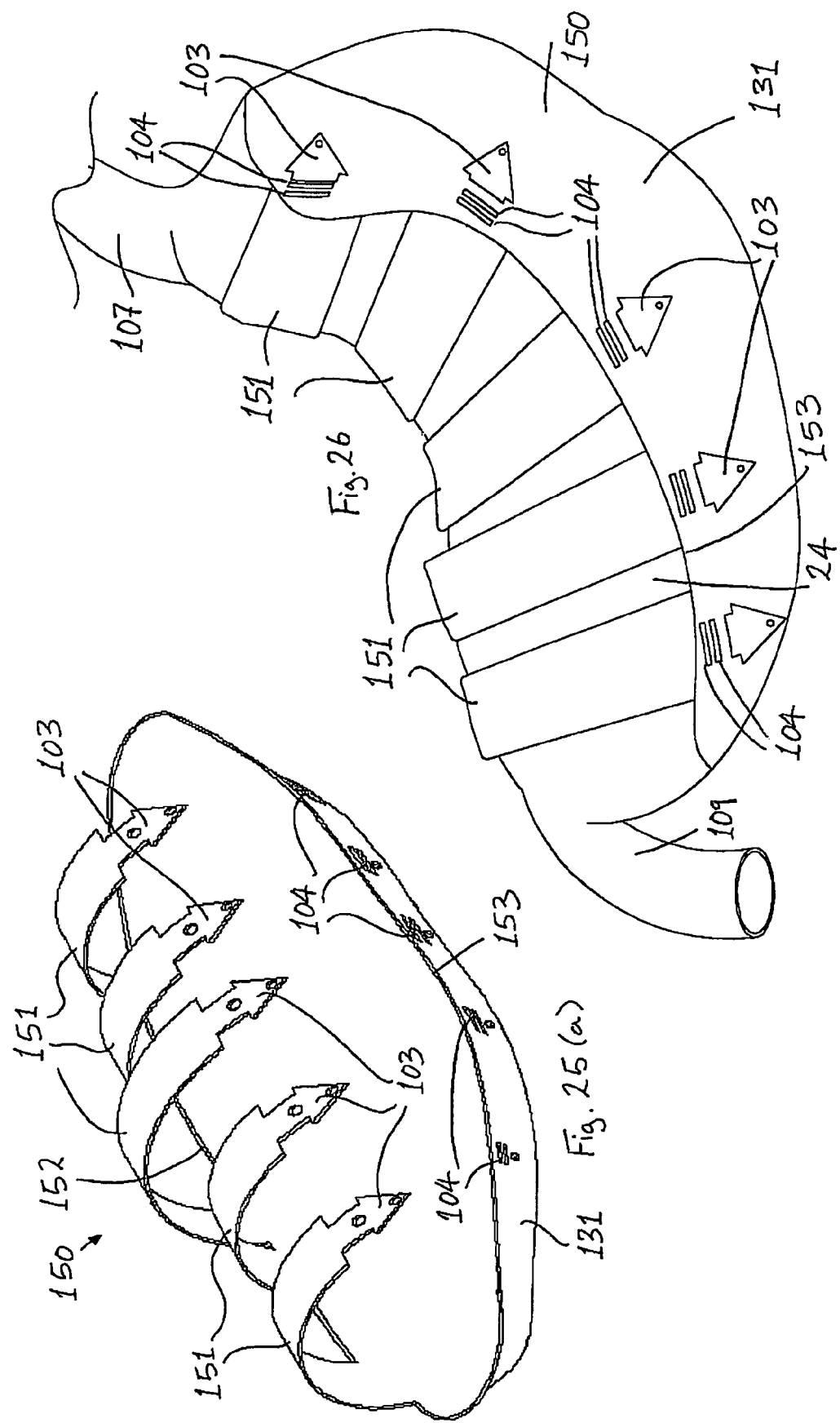

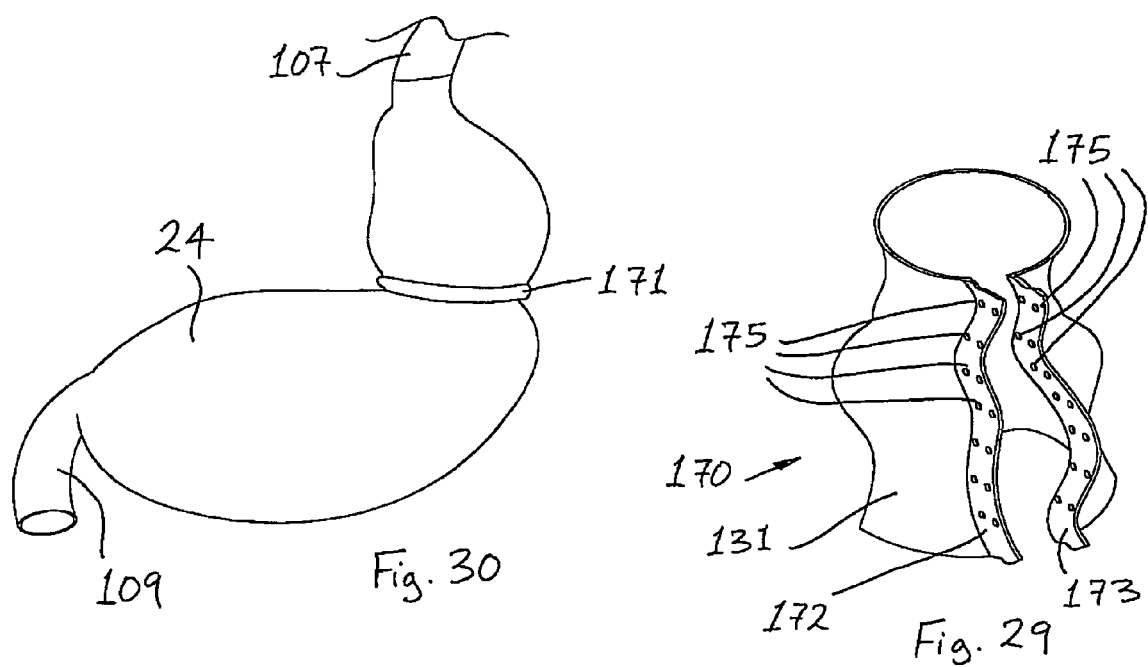

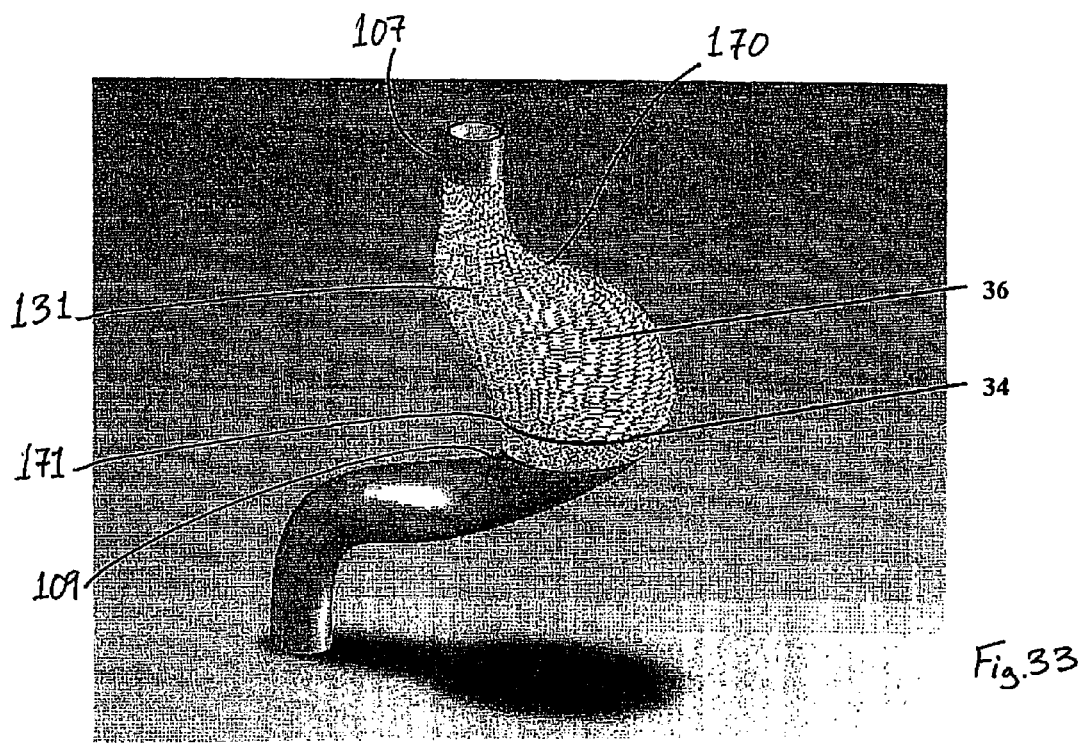
Fig. 33
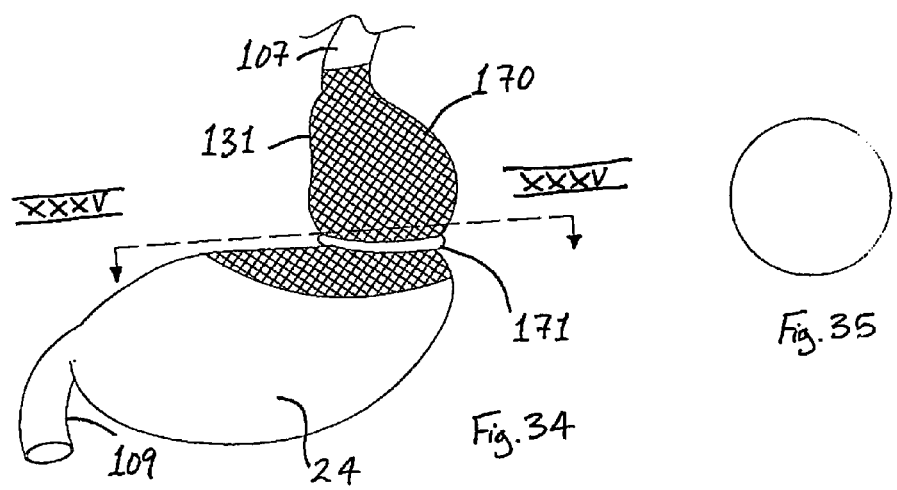
Fig. 34
Fig. 35

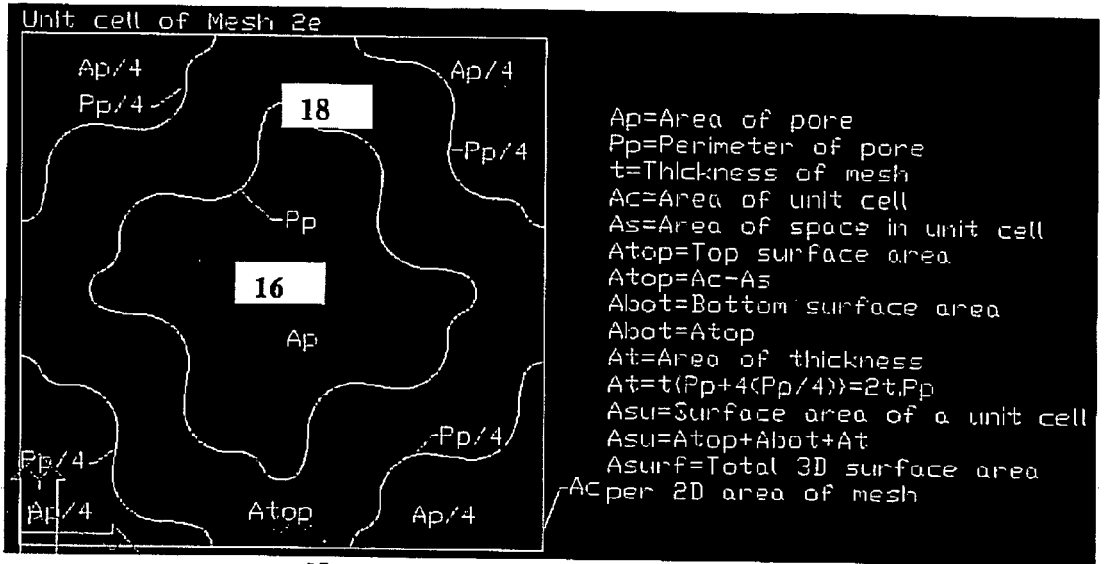

Non-woven Soft Tissue Implant Mesh2E

Fig. 41

Method for Calculating Mesh2E Surface Area

| Area of pore | Ap | 2.78 | mm2 |
|---|---|---|---|
| Perimeter of pore | Pp | 7.83 | mm |
| Thickness | t | 0.20 | mm |
| Area of unit cell | Ac | 10.24 | mm2 |

| Area of space in unit cell | As=Ap+4(Ap/4)=2Ap | 5.56 | mm2 |
|---|---|---|---|
| Top surface area | Atop=Ac-As | 4.68 | mm2 |
| Bottom surface area | Abot=Atop | 4.68 | mm2 |
| Area of thickness | At=t(Pp+4(Pp/4)) | 3.13 | mm2 |

| 3D surface area of a unit cell | Asu=Atop+Abot+At | 12.49 | mm2 |
|---|---|---|---|
| Surface area ratio | Asurf=Asu/Ac | 1.22 | |

Fig. 42

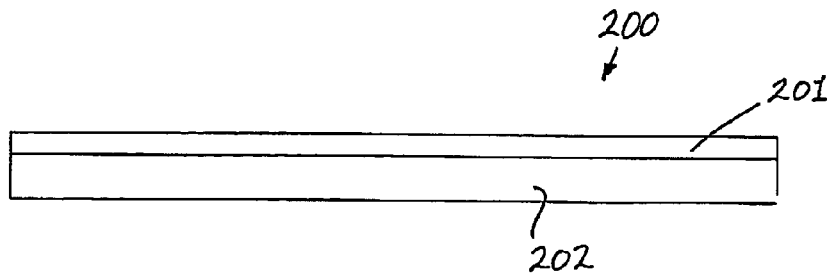
Fig. 45
Fig. 46
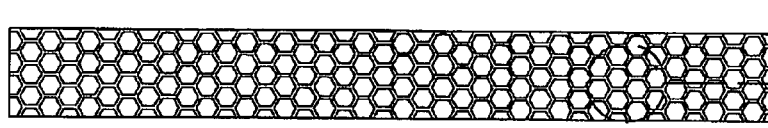
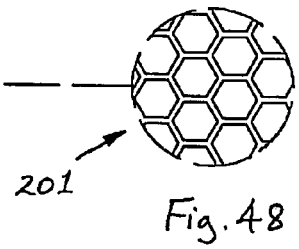
Fig. 47
Fig. 48
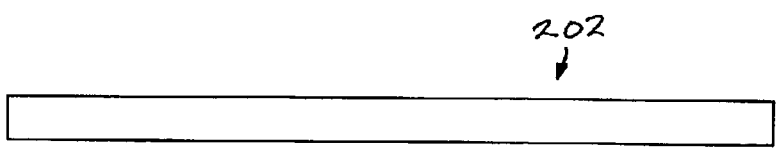
Fig. 49
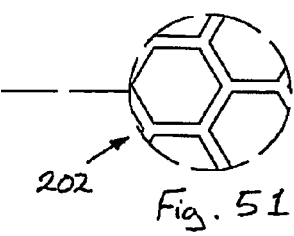
Fig. 50
Fig. 51

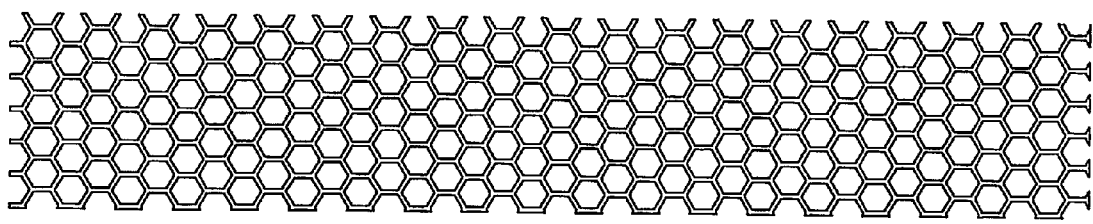
Fig. 52  210
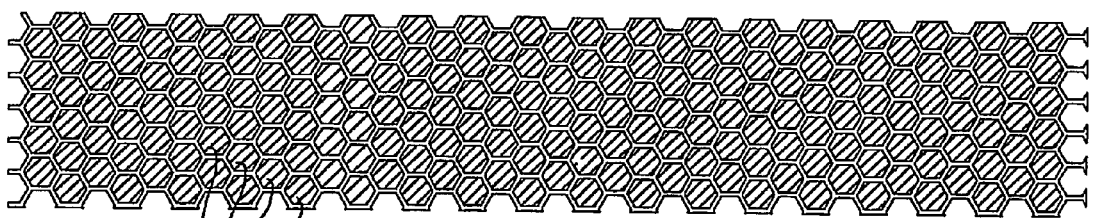
221  220  Fig. 53

Method for producing gastric harness implant

GASTRIC CONSTRICTION DEVICE

This application claims the benefit of U.S. Provisional Application No. 60/514,212, filed Oct. 23, 2003, the content of which is hereby incorporated by reference.

INTRODUCTION

This invention relates generally to a gastric constriction device, and more specifically to gastric implants that can be used to treat obese patients. In particular the invention relates to mechanical systems for treating morbid obesity, especially to devices that interface mechanically with a patient's digestive system in order to restrict food intake.

BACKGROUND

Obesity is a major public health challenge and financial burden for most industrialised countries. In the United States, the healthcare costs for treating obesity reached more than $238 billion in 1999. The Centers for Disease Control and Prevention estimates that nearly 40 million American adults (about 20% of the adult population) are obese. The prevalence of obesity in the United States increased from 12% in 1991 to 19.8% in 2000. The situation is similar in European countries, where 10-20% of the men and 10-25% of the women are obese. "Clinically severe obesity," defined, as being 100 or more pounds overweight, is associated with a number of serious and life-threatening health problems including diabetes, heart disease, respiratory problems, hypertension, gastroesophageal reflux disease, stress urinary incontinence, infertility, osteoarthritis, and some cancers. Conservative treatment, such as dieting, exercise and lifestyle changes, typically fails, making surgery the only hope for these patients. The surgical procedures are designed to restrict the size of the stomach so that food intake is limited and/or bypass steps in the normal digestive process (such as by connecting the stomach to a lower segment of the small intestine) so that food is either poorly digested or is rapidly passed. The National Institute of Health consensus conference in 1991 established widely accepted guidelines and indications for the surgical management of severe obesity (see Gastrointestinal Surgery for Severe Obesity: National Institutes of Health Consensus Development Conference Statement. Am J Clin Nutr 1992; 55: 615S-9S). Surgical methods currently in use are described below.

The relationship of gastric accommodation and satiety in obese individuals has been studied (see Independent Influences of Body Mass and Gastric Volumes on Satiation in Humans. Gastroenterology 2004; 126: 432-440). Increased body mass index has been associated with delayed satiation. Overweight and obese subjects ingest more at maximum satiation compared with normal weight individuals. Increased fasting gastric volume, however, was not associated with body mass index. Chemoreceptors and mechanoreceptors in the stomach wall signal satiation through vagal and splanchnic nerves. When the stomach is relaxed (increased volume at a constant pressure) within the physiological range, it requires higher increases in gastric pressure to activate stretch/tension receptors and thus induce symptoms such as satiation. Data suggests that satiation signals that inhibit ingestion are reduced with increased body mass and that is not due to increased capacity or the stomach's relaxation response to feeding. It has also been determined that the fasting volume of the distal stomach is greater in obese than control subjects (see Is There a Role for Gastric Accommodation and Satiety in Asymptomatic Obese People?. Obesity Research 2001; 9(11): 655-661). Gastric distention with eating contributes to the feeling of fullness or satiation. The mechanism is unclear, but distending the stomach stimulates gastric stretch receptors, which trigger vagal discharges that activate hypothalamic neurons and induce the feeling of satiety. Peptides like leptin, cholecystokinin, and glucagons-like peptide 1 have been shown to evoke satiety, thereby reducing food intake.

The Roux-en-Y gastric bypass is used for surgical treatment of morbid obesity. This involves the partitioning the upper stomach with a surgical stapler and creating a 15 cc intact pouch along the lesser curvature of the stomach. After bypassing a 100 cm section of the bowel, the small intestine is attached to the gastric pouch.

Vertical banded gastroplasty is a simpler operation that involves only the creation of a gastric pouch but does not require extensive surgery of the small intestine. In this procedure, biomaterials that are sutured around the lumen to control stoma size and prevent late stretching of the opening. Biomaterials that are currently used for this procedure include Bard Mesh (C. R. Bard, Inc., Cranston, R.I., USA) and PeriStrips (Biovascular, Inc., St. Paul, Minn., USA).

Another technology used in bariatric surgery is laparoscopic banding. Gastric bands are commonly used to facilitate a reduction in food consumption. The bands are placed around the upper part of the stomach to create a small gastric pouch that limits food consumption and creates an earlier feeling of fullness. Some bands are inflated with saline and connected to an access port placed close to the skin that allows the band to be adjusted. Although the devices are intended to remain in place permanently, the procedure is completely reversible and does not require transection or stapling of the stomach and re-routing of the gastrointestinal tract.

Gastric bands have been developed and are commercially available. For example, Lap-Band™ is an implant that is made from silicone (Inamed, Santa Barbara, Calif., USA; see also U.S. Pat. No. 5,074,868; U.S. Pat. No. 5,226,429; U.S. Pat. No. 5,449,368; U.S. Pat. No. 5,910,149). The SAGB™ or Swedish Adjustable Gastric Band (Obtech Medical AG, Zug, Switzerland) is an inflatable device made of silicone reinforced with a textile.

Gastric pouches were developed by Wilkinson (see U.S. Pat. No. 4,403,604; U.S. Pat. No. 5,246,456). Gastric reservoir reduction was accomplished by wrapping the stomach with an inert fabric. The purported advantages of the gastric pouch include maintenance of restricted size, early satiety with eating, and passage of food through the whole intestine. Gastric wrapping has been shown to create excess body mass index loss of 49, 66, 73, and 66 percent at 6, 12, 24 and 60 months respectively (see A Comparison of the Gastric Bypass and the Gastric Wrap for Morbid Obesity. Surg. Gynecol. Obstet. 1993; 176: 262-266).

Electrical pacing has been applied with benefit in many areas of surgery. In the treatment of obesity, gastric myoelectric stimulation has been shown to produce satiety. Gastric pacing has been shown to create excess body mass index loss of 18.8, 24.1, 22.3, and 32.6 percent at 6, 12, 24 and 60 months respectively (see Gastric Pacing as Therapy for Morbid Obesity: Preliminary Results. Obesity Surgery 2002; 12: 12S-16S).

Each of the implants and procedures presently in use has one or more deficiencies. For example, their construction can result in characteristics that increase the risk of leakage, acute gastric dilatation, wound infection/seroma, obstruction, stoma narrowing/stenosis (with persistent vomiting), ulcer, band slippage or erosion, reservoir deflation/leak, anaemia, calcium deficiency/osteoporosis, and vitamin and mineral deficiencies. Additional disadvantages include the presence of a foreign body, possible difficulties with reversibility if needed, and the increased operative time required to complete the more difficult procedures. The procedures described above can also result in extended patient stay in the hospital due to the invasive nature of the procedures. Also, there is a 19% risk of incisional hernia post-operatively when the procedure is performed by open surgical techniques.

Accordingly, there remains a need for implants for treating obese patients and methods of making those implants.

SUMMARY

According to the invention there is provided a gastric constriction device for constricting the volume of a stomach, the device comprising a material for extending over at least part of the wall of a stomach to constrict the volume of the stomach, the device being configured to restrict expansion of a first region of the stomach wall and to facilitate expansion of a second region of the stomach wall.

In one embodiment the constricting properties of the device vary over at least part of the device. The material may be configured to extend partially around a stomach to restrict expansion of the first region of the stomach wall over which the material extends, and to facilitate expansion of the second region of the stomach wall which remains uncovered by the material. The material may be configured to extend substantially circumferentially partially around a stomach.

In one case the material comprises a sheet. The sheet may be substantially planar.

In one embodiment the sheet is configured to extend over only part of the wall of a stomach.

In another embodiment the sheet is configured to extend over substantially the entire wall of a stomach to enclose the stomach.

The constricting properties of the sheet may vary over the area of the sheet.

The device may comprise a fixation arrangement for fixing the sheet in position extending over at least part of the wall of a stomach. In one case a first region of the sheet is configured to be fixed to a second region of the sheet to fix the sheet in position extending over at least part of the wall of a stomach. The fixing arrangement may comprise at least one band for extending from a first region of the sheet partially around a stomach to a second region of the sheet. The band may be releasably fixed to the second region of the sheet. In one case the fixation of the band to the second region of the sheet is adjustable.

In one embodiment the device comprises a first opening to accommodate an oesophagus and a second opening to accommodate a pylorus. The sheet may be substantially shell-shaped.

According to another aspect, the invention provides a gastric constriction device for constricting the volume of a stomach, the device comprising a band for extending at least partially around a stomach in a spiral to constrict the volume of the stomach. The band may be a spiral band. The band may in one case be pre-formed as a spiral.

The band may be substantially elongated.

In one case at least one spiral turn at least partially overlaps an adjacent spiral turn.

The device may comprise a fixation arrangement for fixing the band in position extending at least partially around a stomach. In one case a first region of the band is configured to be fixed to a second region of the band to fix the band in position extending at least partially around a stomach. The first region may be located at an end of the band, and the second region may be located at an opposite end of the band. The first region may be located at an end of the band, and the second region may be located intermediate the ends of the band.

The invention also provides in another aspect a gastric constriction device for constricting the volume of a stomach, the device comprising a bio-absorbable material for absorption of at least some of the material into the stomach wall over time.

The device may be configured for absorption of substantially all of the device into the stomach wall over time. The absorption properties of the material may vary over the material. The absorption properties in one case vary through the depth of the material. In another case, the absorption properties vary across the area of the material.

The material may be at least partially of a laminate construction. In one case the material comprises a first layer and a second layer, the first layer having a higher absorption rate than the second layer. The first layer may be located adjacent to the second layer. The second layer may be configured to be located closer to a stomach wall than the first layer.

In one embodiment the material is at least partially porous to promote tissue in-growth. The first layer may have a higher pore density than the second layer. The first layer may have a smaller pore size than the second layer. In one case at least some of the pores form at least a partial gradient.

The material may comprise an anti-adhesion filler filling at least some of the pores. The material may comprise an anti-adhesion coating along at least part of the surface of the material.

In another case the material comprises a film.

The device may comprise a band for extending at least partially around a stomach to constrict the volume of the stomach. In one case the band is substantially elongated.

In another case the band comprises a loop band for extending at least partially around a stomach in a loop. The device may comprise a plurality of loop bands for extending at least partially around a stomach at a plurality of regions along the stomach. Each loop band may be disconnected from an adjacent loop band. At least one loop band may at least partially overlap an adjacent loop band.

In another embodiment the band is configured to be extended at least partially around a stomach in a spiral. The band may be a spiral band. The band may be pre-formed as a spiral.

At least one spiral turn may at least partially overlap an adjacent spiral turn.

In one case the device comprises a fixation arrangement for fixing the band in position extending at least partially around a stomach. A first region of the band may be configured to be fixed to a second region of the band to fix the band in position extending at least partially around a stomach. In one case the first region is located at an end of the band, and the second region is located at an opposite end of the band. In another case the first region is located at an end of the band, and the second region is located intermediate the ends of the band.

In a further embodiment the device comprises a sheet for extending over at least part of the wall of a stomach to constrict the volume of the stomach. The device may be configured to restrict expansion of a first region of a stomach wall and to facilitate expansion of a second region of the stomach wall.

The constricting properties of the device may vary over at least part of the device.

In another embodiment the material is configured to extend partially around a stomach to restrict expansion of the first region of the stomach wall over which the material extends, and to facilitate expansion of the second region of the stomach wall which remains uncovered by the material. The material may be configured to extend substantially circumferentially partially around a stomach.

In one case the constricting properties of the sheet vary over the area of the sheet.

The sheet may be configured to extend over only part of the wall of a stomach. The sheet may be configured to extend over substantially the entire wall of a stomach to enclose the stomach.

In one case device comprises a fixation arrangement for fixing the sheet in position extending over at least part of the wall of a stomach. A first region of the sheet may be configured to be fixed to a second region of the sheet to fix the sheet in position extending over at least part of the wall of a stomach. The fixing arrangement may comprise at least one band for extending from a first region of the sheet partially around a stomach to a second region of the sheet. The band may be releasably fixed to the second region of the sheet. In one case the fixation of the band to the second region of the sheet is adjustable.

In another embodiment the device comprises a first opening to accommodate an oesophagus and a second opening to accommodate a pylorus.

In one case the sheet is substantially shell—shaped.

The device may comprise a gastric nerve stimulator.

In a further aspect, the invention provides a gastric constriction device for constricting the volume of a stomach, the device comprising a material for extending over at least part of the wall of a stomach to constrict the volume of the stomach, wherein the device comprises a gastric stimulator. The gastric stimulator may comprise a gastric nerve stimulator.

The invention also provides in a further aspect a gastric constriction device for constricting the volume of a stomach, the device comprising a sheet for extending over at least part of the wall of a stomach to constrict the volume of the stomach, and a band for extending at least partially around the stomach to constrict the volume of the stomach.

The band may be configured to be located between the sheet and the wall of a stomach.

According to another aspect, the invention provides a gastric constriction apparatus comprising:—
 a gastric constriction device of the invention; and
 a collapsing device at least partially insertable into the interior of a stomach to at least partially collapse the stomach from a normal volume to a reduced volume.

The collapsing device may comprise a suction device to at least partially collapse a stomach by applying suction to the interior of the stomach.

In one case the collapsing device comprises a sealing member for sealing the entry to a stomach at the oesophagus. The collapsing device may comprise a sealing member for sealing the exit from a stomach at the pylorus. The sealing member may be inflatable.

The invention also provides in a further aspect a method of constricting the volume of a stomach, the method comprising the steps of:
 applying a collapsing force to the stomach to at least partially collapse the stomach from a normal volume to a reduced volume;
 positioning a gastric constriction device relative to the stomach; and
 releasing the collapsing force;
 the gastric constriction device then applying a constricting force to the stomach to constrict the volume of the stomach.

The method may comprise the step of inserting a collapsing device at least partially into the interior of the stomach before applying the collapsing force. The collapsing force may be applied by applying suction to the interior of the stomach. In one case the method comprises the steps of sealing the entry to the stomach at the oesophagus before applying suction. The method may comprise the step of sealing the exit from the stomach at the pylorus before applying suction. In one case the sealing is effected by inflating a sealing member. The collapsing force may be released by releasing suction of the interior of the stomach.

In one embodiment the gastric constriction device is positioned extending at least partially around the stomach. The gastric constriction device may be positioned extending at least partially around the stomach in a loop. The gastric constriction device may be positioned extending at least partially around the stomach in a spiral.

In another embodiment the gastric constriction device is positioned extending over at least part of the wall of the stomach. The gastric constriction device may be positioned extending over only part of the wall of the stomach.

The gastric constriction device may be positioned extending over substantially the entire wall of the stomach to enclose the stomach.

In a further embodiment a first part of the gastric constriction device is positioned extending at least partially around the stomach, and a second part of the gastric constriction device is positioned extending over at least part of the wall of the stomach. The first part may be positioned between the second part and the wall of the stomach.

The method may comprise the step of fixing the gastric constriction device in position relative to the stomach.

The method may comprise the step of adjusting the constricting force applied to the stomach.

In one case the gastric constriction device restricts expansion of a first region of the stomach wall and facilitates expansion of a second region of the stomach wall.

In a further embodiment the method comprises the step of stimulating gastric nerves.

The invention provides in another aspect a method of treating obesity comprising the steps of:
 constricting the volume of a stomach; and
 stimulating gastric nerves The step of constricting the volume of the stomach may comprise a method of the invention.

The invention provides in one case a bariatric surgical method.

The present invention features a gastric harness implant that includes a biocompatible film. The film has a thickness of less than about 0.500 inches for non-porous films and less than 1.000 inches for microporous films. A given implant can include more than one film (e.g., more than one porous biocompatible film); for example, the invention features an implant that includes a first porous biocompatible film and a second porous biocompatible film, the thickness of the implant being less than about 1.000 inches. The implants, including the materials from which they are made and the cell patterns they can contain are described further below. It is not necessary to remove the gastric harness of the invention. The gastric harness can be produced with biodegradable materials that are resorbed by the body.

The implant is produced by processing a biocompatible polymer into a film and forming pores in the film. In alternative embodiments, the film can be stretched or otherwise manipulated (e.g., trimmed, shaped, washed or otherwise treated) before or after forming pores in the film. Where the implant contains more than one film, the methods of the invention can be carried out by extruding a first biocompatible polymer to form a first film, extruding a second biocompatible polymer to form a second film, attaching the first film to the second film to produce a implant, and forming pores in the implant. Alternatively, the pores can be formed before the two films are adhered to one another. In that instance, the method of making the implant can be carried out by: extruding a first biocompatible polymer to form a first film; forming pores in the first film; extruding a second biocompatible polymer to form a second film; forming pores in the second film; and attaching the first film to the second film to produce a gastric harness implant.

Where the implant contains more than one film, the methods of the invention can be carried out by extruding a first biocompatible polymer to form a first film, extruding a second biocompatible polymer to form a second film, attaching the first film to the second film to produce a implant, and forming pores in the implant. The pores can be formed before the two films are adhered to one another. The pores can have different dimensions, the films can have different thicknesses, and the films can have different compositions all of which vary the healing and biodegradation characteristics. In that instance, the method of making the implant can be carried out by: extruding a first biocompatible polymer to form a first film; forming pores in the first film; extruding a second biocompatible polymer to form a second film; forming pores in the second film; and attaching the first film to the second film to produce a gastric harness implant. The gastric harness implant can be designed with controlled tissue ingrowth and remodelling to permanently alter the tissue and mechanical properties of the stomach.

Where a film is obtained, rather than made, the methods of making the implant can simply require providing a given film that is then attached (e.g., reversibly or irreversibly bound by mechanical or chemical forces), if desired, to another film and/or processed to include one or more pores of a given size and arrangement. The single provided film (or adherent multiple films) can then be subjected to a process (e.g., laser ablation, die punching, or the like) that forms pores within the film(s). Accordingly, any of the methods of the invention can be carried out by providing a given biocompatible film, rather than by producing it by an extrusion or extrusion-like process.

The films can also be produced using casting, injection moulding or dip coating techniques.

Preferably, the gastric harness implants of the invention will include (or consist of) a film that has a low profile (or reduced wall thickness) and that is biocompatible. A biocompatible film is one that can, for example, reside next to biological tissue without harming the tissue to any appreciable extent. As noted above, the film(s) used in the implants of the invention can have pores (e.g., open passages from one surface of the film to another) that permit tissue ingrowth and/or cellular infiltration.

The implants of the present invention offer a combination of high porosity, high strength, and low material content, and they may have one or more of the following advantages. They can include pores or porous structures that stimulate fibrosis and reduce inflammation; they can reduce the risk of erosion and formation of adhesions with adjacent tissue (this is especially true with implants having a smooth surface and atraumatic (e.g., smooth, tapered, or rounded edges); they can simulate the physical properties of the tissue being repaired or replaced, which is expected to promote more complete healing and minimise patient discomfort; their surface areas can be reduced relative to prior art devices (having a reduced amount of material may decrease the likelihood of an immune or inflammatory response). Moreover, implants with a reduced profile can be produced and implanted in a minimally invasive fashion; as they are pliable, they can be placed or implanted through smaller surgical incisions. The methods of the invention may also produce implants with improved optical properties (e.g., implants through which the surgeon can visualise underlying tissue). Practically, the micromachining techniques that can be used to produce the implants of the present invention are efficient and reproducible. The implants described herein should provide enhanced biocompatibility in a low profile configuration while maintaining the requisite strength for the intended purpose.

The biocompatible films described above can be used to construct gastric harness implants that are designed to engage the outer surface of the stomach to reduce tension when food is consumed. The implant can be configured to encircle the stomach to act as a gastric harness. Ideally, the implant is inserted laparoscopically using minimally invasive techniques and instrumentation. The invention also features methods for producing gastric harness implants. These methods can include the step of applying a shape memory material, for example an alloy, such as nitinol, to the gastric harness implant to facilitate sizing, attachment, and implantation. The gastric harness implant can also be fabricated from a shape memory polymer (mnemoScience GmbH, Aachen, Germany).

The overall shape of the implants can vary depending on the size of the individual and the stomach to be restricted. The overall length, width, and shape of the implants of the present invention can be designed to impart a certain volume to the restricted stomach. Once the volume limit of the stomach is reached, the shaped gastric harness implant prevents an increase in tension on the stomach wall with the associated volume increase. This volume limit is typically approximately 15 cc or higher.

Because the volume of the stomach is determined at the time of surgery, the need to adjust the gastric harness implant is reduced. In addition, the gastric harness implant is in contact with a large area of the stomach, which reduces the potential for implant slippage. In one embodiment of the invention, the gastric harness implant consists of separate panels that are positioned individually to restrict the stomach. In another embodiment, the gastric harness implant consists of a strip of biocompatible material that is wrapped continuously around the stomach. In another embodiment, the gastric harness implant can be used in conjunction with a gastric banding device to restrict the size of the gastric pouch that is formed with the band. In addition, the gastric harness implant will reduce the size of the access incision with a laparoscopic or minimally invasive approach to help reduce peripoperative morbidity and to speed recovery. The improvements will come without creating a procedure that is too complex.

A further embodiment of the invention is to produce the gastric harness implant with variable elasticity such that certain areas of the implant expand more under pressure or load. In this instance, a feeling of satiety may be created by placing the more elastic zones adjacent to nerves that are responsible for signalling with increases in gastric pressure to activate stretch/tension receptors and thus induce symptoms such as satiation. The gastric implant may also be designed to wrap the stomach in select areas where the nerves responsible for signalling are not present. Therefore, the stomach would be constrained in certain areas that are not responsible for signalling. An early feeling of satiety would be realised due to preferential expansion and creation of stomach wall tension in the areas where the gastric harness is not present. Vagal nerves would be activated more readily creating a feeling of satiety.

A further embodiment of the invention is to produce the gastric implant from a bioresorbable or biodegradable material. The bioresorbable or biodegradable implant will stay in position and restrict the stomach volume over a predetermined time. The mechanical strength and shape of the gastric implant will restrict the stomach for the predetermined time. The gastric harness implant will create weight loss for the patient over the predetermined time period. After the predetermined time the gastric harness implant will be absorbed, and the implant will no longer be a risk for chronic wound complications. In this case a second procedure to remove the implant will not be required.

This invention provides an implant device comprising a biocompatible material that is configured to provide a gastric harness to constrain the volume of the stomach. The harness may be configured to conform generally to a patient's stomach. The harness may extend from the oesophagus to the small intestine.

In one embodiment the harness defines an internal volume between an upper end and a lower end, which conforms generally to the external geometry of the stomach to constrain circumferential expansion of the stomach beyond a maximum adjusted volume during eating/digestion.

The gastric harness can be used in conjunction with laparoscopic bands. In one embodiment the harness defines an internal volume between an upper end of the stomach and a gastric band, which conforms generally to the external geometry of the stomach pouch to constrain circumferential expansion of the stomach pouch beyond a maximum adjusted volume during eating/digestion.

In one embodiment the harness defines a means for accepting a gastric pacing device. The harness defines an internal volume between an upper end and a lower end, which conforms generally to the external geometry of the stomach to constrain circumferential expansion of the stomach beyond a maximum adjusted volume during eating/digestion. In addition, the gastric pacing device creates a feeling of satiety in the patient.

The biocompatible material may comprise a biocompatible film, which can be of laminate construction. The film may be non-porous or may be microporous.

In one embodiment the biocompatible material comprises polypropylene, polyethylene terephthalate, polytetrafluoroethylene, polyaryletherketone, nylon, fluorinated ethylene propylene, polybutester, or silicone.

In another embodiment the biocompatible material is biodegradable. The biocompatible material may be at least partially absorbable by the body. The biocompatible material may comprise an absorbable polymer or copolymer such as polyglycolic acid (PGA), polylactic acid (PLA), polycaprolactone, or polyhydroxyalkanoate.

The porous biocompatible film may comprise a biological material such as collagen.

The porous biocompatible film used to construct the implant may comprise an adhesion prevention material such as hyaluronic acid. The adhesion prevention material can either coat the porous film or fill the pores. The adhesion prevention material may degrade as surrounding tissue heals and minimises the risk of future adhesions.

In one embodiment the biocompatible material has a plurality of cells. The biocompatible material may have a plurality of cells and one or more of the cells in the plurality of cells has a diameter, measured along the longest axis of the cell, of about 10 to about 10,000 microns. The biocompatible material may have a plurality of cells and one or more of the cells of the plurality are essentially square, rectangular, sinusoidal, or diamond-shaped. One or more of the cells of the plurality may be substantially the same shape as the cell shown in Mesh2E.

In one embodiment each of the cells in the plurality of cells has a plurality of undulating elements in the form of a repeating pattern. The undulating elements may be in phase and the force-displacement characteristics may restrict stomach expansion. Typically the plurality of cells has a diameter greater than 50 microns and the implant has force displacement characteristics that restrict tissue movement in a controlled manner.

In one embodiment the thickness of the porous biocompatible film is less than about 0.014 inches, less than about 0.013 inches, less than about 0.012 inches, less than about 0.011 inches, less than about 0.010 inches, less than about 0.009 inches, less than about 0.008 inches, less than about 0.007 inches, less than about 0.006 inches, less than about 0.005 inches, less than about 0.004 inches, less than about 0.003 inches, less than about 0.002 inches or about 0.001 inch.

In one embodiment the thickness of the porous biocompatible film is less than about 0.500 inches. The porous biocompatible film can be formed from multiple porous films less than about 0.014 inches, less than about 0.013 inches, less than about 0.012 inches, less than about 0.011 inches, less than about 0.010 inches, less than about 0.009 inches, less than about 0.008 inches, less than about 0.007 inches, less than about 0.006 inches, less than about 0.005 inches, less than about 0.004 inches, less than about 0.003 inches, less than about 0.002 inches or about 0.001 inch.

In one embodiment the restricted stomach volume is 10 cc or greater.

The harness may comprise attachment regions, which may be adapted to receive sutures, staples or the like.

The harness may comprise a fastener such as sutures for fastening the harness in position in use.

In one embodiment the biocompatible material is in the form of a strip for winding around a patient's stomach. The strip may have attachment points. The strip may form a circular band at the top of the stomach near the oesophagus and at the bottom near the pylorus. The circular bands prevent slippage and provide a smooth interface with the stomach to prevent erosion. The central portion of the strip is wrapped around the stomach in a circular fashion and is spaced such that the stomach will not distend through the spacings when food is ingested. The strip can be preformed and set to have three-dimensional qualities to facilitate sizing and placement around the stomach.

In one embodiment the biocompatible material is in the form of individual strips for placement around a patient's stomach. The strips may have attachment points. The strips may form circular bands from the top of the stomach near the oesophagus to the bottom near the pylorus. The individual strips can be placed and spaced evenly in a manner that accommodates different individual's anatomy. The circular bands provide a smooth interface with the stomach to prevent erosion. The individual strips are spaced such that the stomach will not distend through the spacings when food is ingested. The strips can be preformed and set to have three-dimensional qualities to facilitate sizing and placement around the stomach.

In another embodiment the implant further comprises a gastric band. The gastric band is of the same material as that of the harness or may be of a different material than that of the harness.

In one embodiment the harness has a support, which may be of a shape memory material such as a shape memory alloy material, for example Nitinol.

In another aspect the invention provides a gastric harness implant device for treating obesity, the device comprising: a biocompatible material configured to engage the (outer) surface of the stomach to relieve tension on the stomach.

In a further aspect the invention provides a biocompatible material forming a gastric harness implant defining an (internal) volume between an upper end and a lower end; said gastric harness implant adapted to be secured to the stomach to snugly conform to the external geometry of the stomach and to constrain circumferential expansion of the stomach beyond a maximum adjusted volume during eating/digestion; an adjustment mechanism; a fastening mechanism.

In another aspect the invention provides a gastric harness implant comprising an implantable material positioned around the stomach to restrict the volume of the stomach.

The biocompatible material may be configured to generally conform to a patient's stomach, the biocompatible material being configured to extend circumferentially around the stomach. The implantable material may be positioned from the oesophagus to the small intestine.

In another aspect the invention provides a method for treating obesity, the method comprising: inserting a balloon into the stomach with a predetermined volume; providing a gastric reinforcement device shaped and configured to engage at least a portion of the patient's stomach and to reduce the volume potential of the stomach; and placing the gastric reinforcement device on the patient's stomach such that said device extends circumferentially around the patient's stomach. The method may include the step of providing a securement means for the device to prevent slippage.

In another aspect the invention provides a method for treating obesity, the method comprising: inserting a gastric tube with or without perforations and with or without a lumen into the stomach with a predetermined volume; applying a vacuum source to the lumen of the gastric tube; providing a gastric reinforcement device shaped and configured to engage at least a portion of the patient's stomach and to reduce the volume potential of the stomach; and placing the gastric reinforcement device on the patient's stomach such that said device extends circumferentially around the patient's stomach. The method may include the step of providing a securement means for the device to prevent slippage.

In one aspect the invention provides a method for treating obesity, the method comprising; surgically accessing the stomach; inserting a balloon into the stomach with a predetermined volume; reducing the size of said stomach; placing a gastric support device on said stomach; securing said gastric support device to said stomach having a reduced size/volume, wherein said gastric support device comprises a biocompatible material configured to constrain expansion of the stomach; surgically closing access to said stomach while leaving said gastric support device in place on said stomach.

In a further aspect the invention provides a method for producing a gastric harness implant, the method comprising: extruding a biocompatible polymer into a film; and forming a plurality of cells in the film; wherein the method may further comprise the optional step of cleaning the implant.

The invention also provides a method for producing a gastric harness implant, the method comprising: extruding a biocompatible polymer into a film, stretching the film; forming pores in the film to produce a soft tissue implant; wherein the method may further comprise the optional step of cleaning the implant.

The invention further provides a method for producing a gastric harness implant, the method comprising: extruding a first biocompatible polymer to form a first film; extruding a second biocompatible polymer to form a second film; attaching the first film to the second film to produce an implant; forming pores in the implant; shaping the implant into a configuration that imparts a known volume to the stomach; attaching a shape memory element to the implant; wherein the method may further comprise the optional step of cleaning the implant.

In another aspect the invention provides a method for producing a soft tissue implant, the method comprising: extruding a first biocompatible polymer to form a first film; forming pores or cell patterns in the first film; extruding a second biocompatible polymer to form a second film; forming pores in the second film; attaching the first film to the second film to produce a soft tissue implant; wherein the method may further comprise the optional step of cleaning the implant.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2 is a perspective view of a gastric constriction device according to the invention;

FIGS. 6 to 8 are perspective views illustrating constricting the volume of the stomach of FIG. 5 using the gastric constriction device of FIG. 2 and the collapsing device of FIG. 4;

FIG. 9 is a view along line IX-IX in FIG. 7;

FIG. 12 is a perspective view of a loop band of the device of FIG. 11 in a release configuration;

FIG. 13 is a perspective view of the loop band of FIG. 12 in a fixed configuration;

FIGS. 14 and 15 are perspective views similar to FIGS. 12 and 13 of a loop band of another gastric constriction device according to the invention;

FIG. 16 is a plan view of an end of the loop band of FIG. 14;

FIG. 17 is a perspective view of a tool suitable for use with the loop band of FIGS. 14 to 16;

FIG. 18 is a perspective view similar to FIG. 12 of a loop band of another gastric constriction device according to the invention;

FIG. 19 is a plan view of an end of the loop band of FIG. 18;

FIG. 20 is a perspective view of another gastric constriction device according to the invention extending over the wall of a stomach to restrict the stomach;

FIG. 21 is a view along line XXI-XXI in FIG. 20;

FIGS. 22 and 23 are perspective views illustrating collapsing the volume of a stomach using the gastric constriction device of FIG. 20 and another collapsing device according to the invention;

FIG. 24 is a view along line XXIV-XXIV in FIG. 23;

FIGS. 25(a) and 25(b) are perspective views of a further gastric constriction device according to the invention;

FIG. 26 is a perspective view of the device of FIG. 25 extending over the wall of a stomach;

FIG. 29 is a perspective view of another gastric constriction device according to the invention;

FIGS. 30 and 31 are perspective views illustrating constricting the volume of a stomach using a loop band according to the invention and the device of FIG. 29;

FIGS. 33 and 34 are perspective views of the gastric harness implant of FIG. 29 used with a gastric banding device;

FIG. 35 is a view along line XXXV-XXXV in FIG. 34;

FIGS. 41 and 42 relate to an implant designated Mesh2E, where FIG. 41 is a diagram of an exemplary pore, and FIG. 42 is a display of various measured parameters within Mesh2E and the equations used to calculate the surface area;

FIG. 45 is a side view of a material of another gastric constriction device according to the invention;

FIG. 46 is a side view of a first layer of the material of FIG. 45;

FIG. 47 is a plan view of the first layer of FIG. 46;

FIG. 48 is an enlarged, plan view of a part of the first layer of FIG. 47;

FIGS. 49 to 51 are views similar to FIGS. 46 to 48 of a second layer of the material of FIG. 45;

FIGS. 52 and 53 are plan views of materials of further gastric constriction devices according to the invention.

Figure 1:
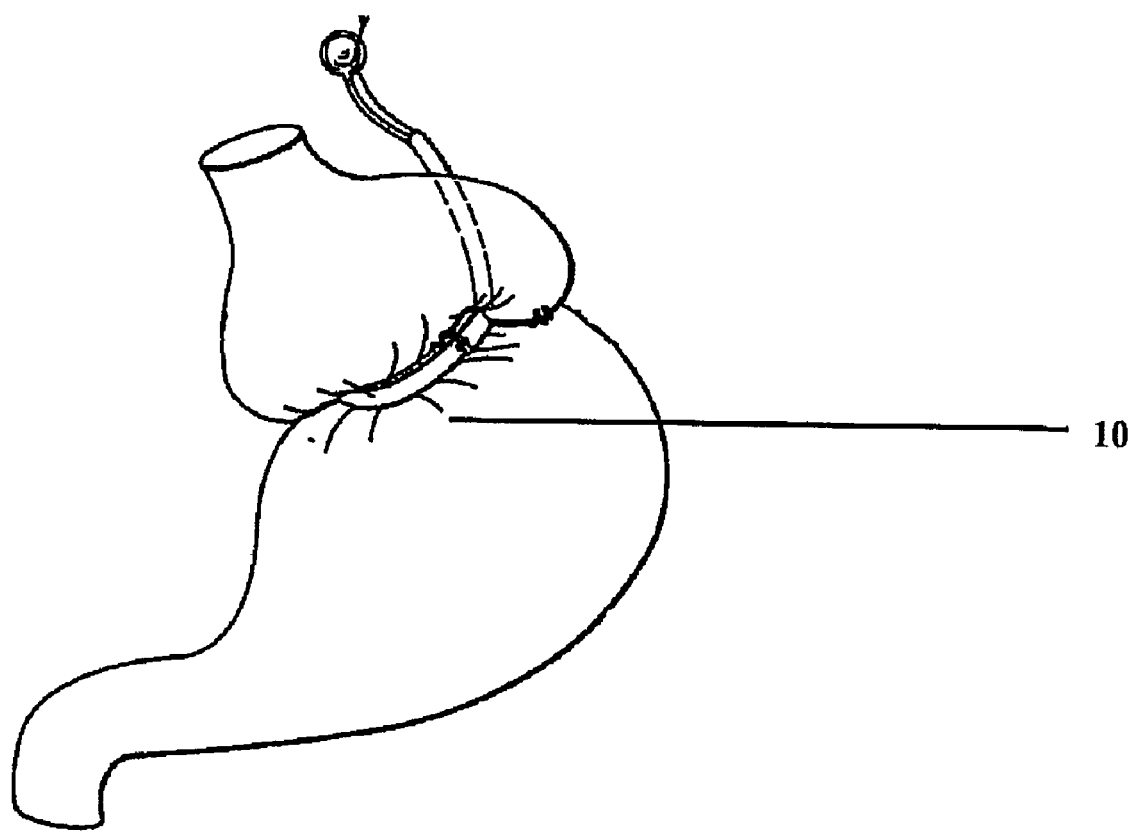
FIG. 1 is a perspective view of a prior art gastric banding device.

SELECTED REFERENCE NUMERALS IN DRAWINGS 10 gastric banding device
12 biocompatible film
14 laminated film structure
16 cell pattern
18 radius
20 cell pattern structure
22 machined film
24 unrestricted stomach
26 gastric harness implant
28 attachment points
32 strip configuration
34 gastric band
36 gastric pouch

DETAILED DESCRIPTION

FIG. 1 illustrates a prior art gastric banding device 10 that can be used to perform gastric banding procedures.

Figure 3:
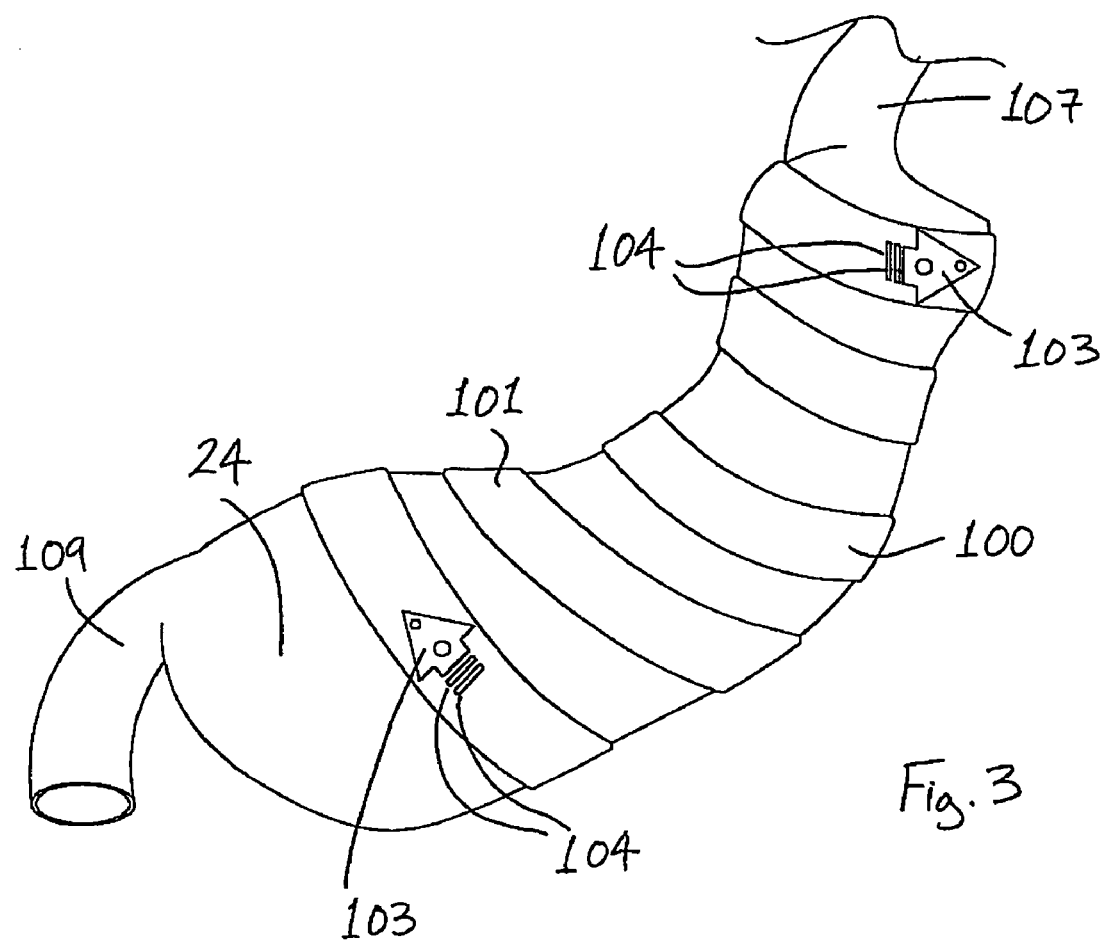
FIG. 3 is a perspective view of the device of FIG. 2 extending around a stomach.

Referring to FIG. 2 there is illustrated a gastric constriction device 100 according to the invention. The device 100 comprises a substantially elongate spiral band 101 which may be extended around a stomach 24 in a spiral to constrict the volume of the stomach 24, as illustrated in FIG. 3.

A fixation arrangement is provided at each end of the band 101. In this case, each fixation arrangement is provided in the form of an arrow-head shaped member 103 at the end of the band 101, which may be received in one of a plurality of corresponding slots 104 in the band 101. As illustrated in FIG. 2, the slots 104 are located spaced a distance from the end of the band 101. The plurality of slots 104 enable a degree of adjustment of the constriction force to be achieved.

It has been found that the spiral wrap of the band 101 may be positioned around the blood vessels of the stomach wall in such an arrangement such as to preserve blood flow.

FIG. 2 illustrates the gastric harness strip 101 in spiral wrap form. The strip material can be preformed with three-dimensional properties and may be made from a shape memory material. The strip 101 can also form bands at the top and bottom for securement near the oesophagus and pylorus. Slits 104 in the strip 101 can be used to create bands. The circular bands prevent slippage and provide a smooth interface with the stomach 24 to minimise the risk of erosion. The central portion is wrapped around the stomach 24 in circular fashion and is spaced such that the stomach 24 will not distend through the spacings when food is ingested.

Multiple slits 104 in the strip 101 can be provided to adjust the diameter of the band. This permits a fit that prevents slippage while minimising the risk of erosion if the band is placed too tightly around the stomach 24. A tapered point 103 on the strip 101 facilitates placement through the slit 104. Holes 300 in the tapered point 103 permit the use of instruments to facilitate grasping. The holes 300 also permit securement if a suture or a staple is used. The width of the tapered securement point 103 is wider than the slit 104 to create a mechanical lock.

Figure 4:
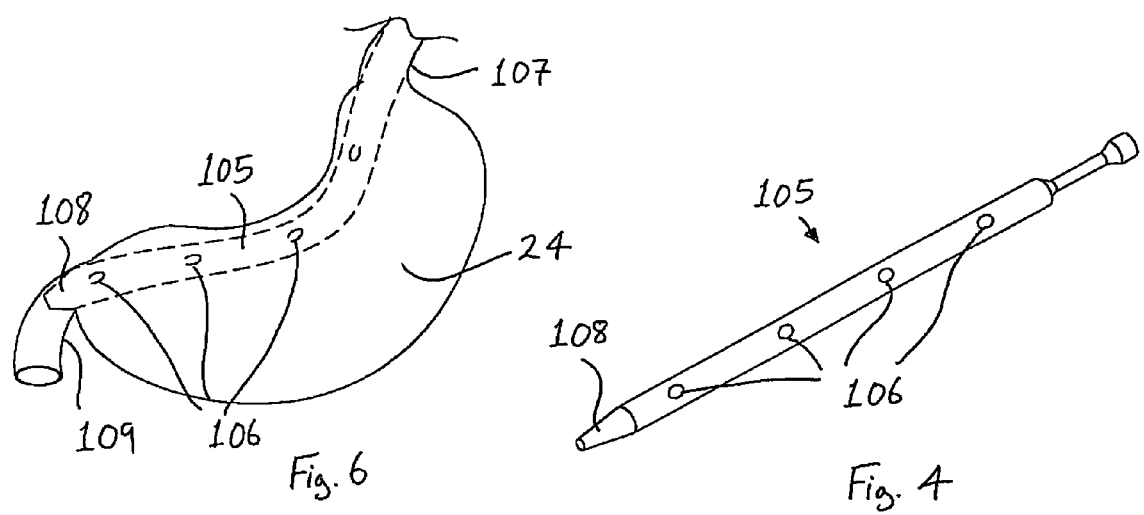
FIG. 4 is a perspective view of a collapsing device according to the invention.
Figure 5:
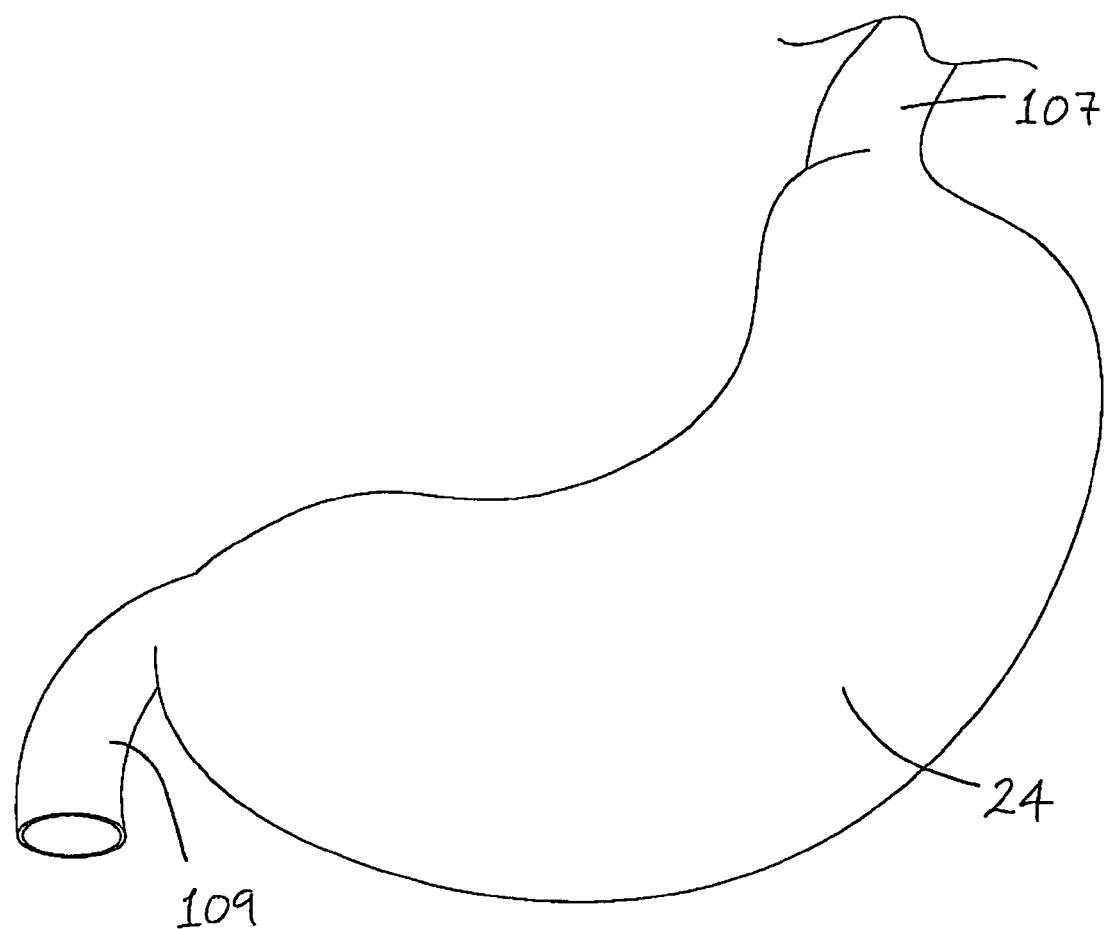
FIG. 5 is a perspective view of an unrestricted stomach.

FIG. 4 illustrates a suction device 105 according to the invention suitable for use with the gastric constriction device 100 to constrict the volume of the stomach 24. Together the suction device 105 and the gastric constriction device 100 provide a gastric constriction apparatus.

The suction device 105 includes a plurality of openings 106 along the length of the suction device 105 for applying suction to the interior of the stomach 24.

With reference to FIGS. 5 to 9, in use the suction device 105 is inserted through the oesophagus 107, into the interior of the unrestricted stomach 24, until the distal tip 108 of the suction device 105 reaches the pylorus 109 (FIG. 6). The suction device 105 engages the tissue wall at the oesophagus 107 and at the pylorus 109 to effect a seal.

Figure 8:
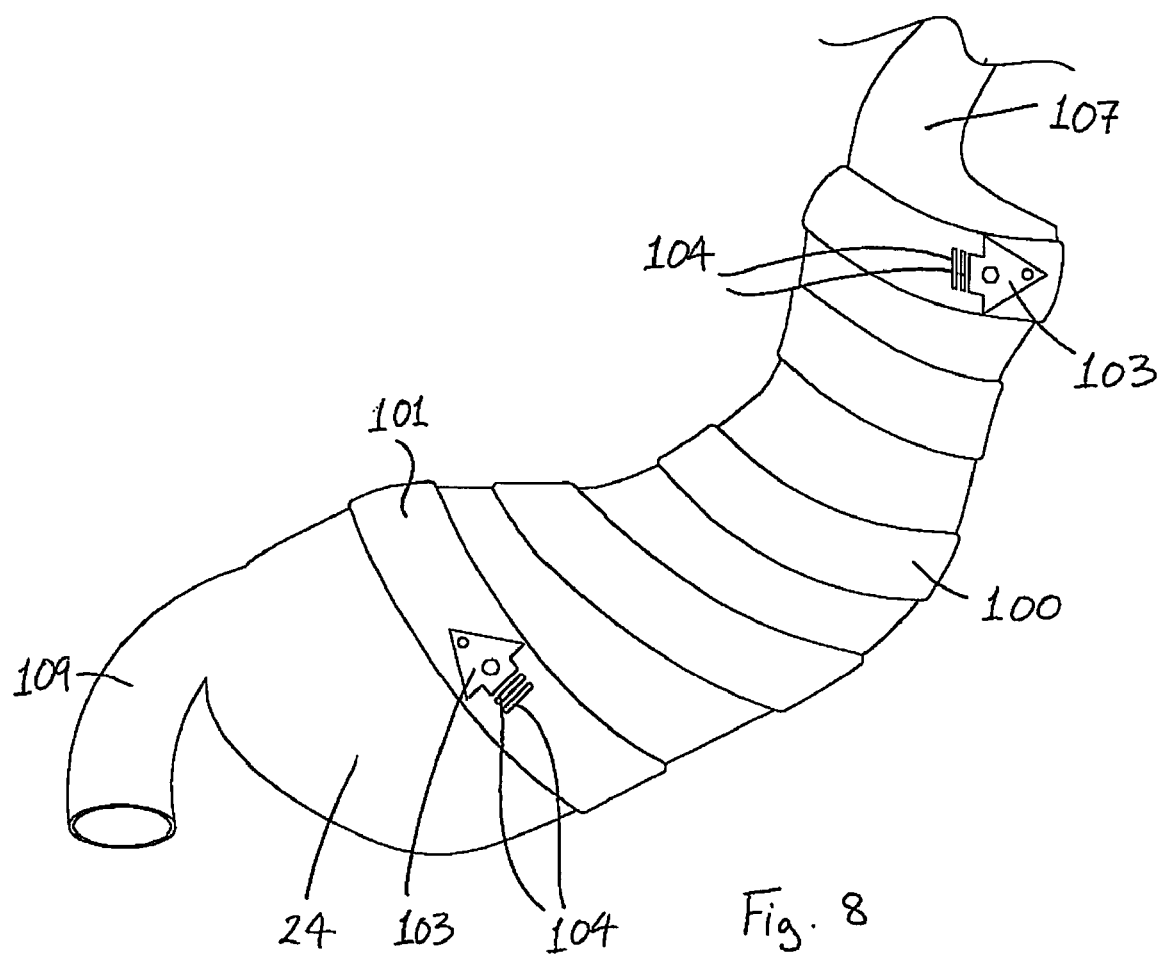

Suction is then applied to the interior of the stomach 24 using the suction device 105. This suction exerts a collapsing force on the stomach 24, and causes the stomach 24 to partially collapse from the normal volume (FIGS. 5 and 6) to a reduced volume (FIGS. 7 and 8). A typical normal volume for the stomach is 750 cc, and a typical reduced volume is 100 cc.

The spiral band 101 is positioned relative to the partially collapsed stomach 24 extending around the stomach 24 in a spiral, and the spiral band 101 is fixed in position by inserting each arrow-head shaped member 103 into a corresponding slot 104 (FIG. 7).

The suction may then be released to release the collapsing force exerted on the stomach 24, and the suction device 105 is removed from the stomach 24 and oesophagus 107. The gastric constriction device 100 remains fixed in position around the stomach 24 constricting the volume of the stomach 24 (FIG. 8).

FIGS. 6 to 8 illustrate the gastric harness with calibrated vacuum assisted deployment. A fixed volume/diameter gastric tube 105 is placed inside the stomach 24 with or without perforations (illustrated with perforations). A means for applying a vacuum is also present. Perforations 106 are positioned inside the stomach 24 and a seal is created at the oesophagus 107 and pylorus 109. The gastric tube 105 may have fixed compliance and volume to replicate the pressure and volume relationship experienced when food is ingested. The gastric harness implant 100 is placed around the stomach 24 with the gastric tube 105 in position. Folds in the stomach wall are created as the surface area in the outer wall is reduced. The gastric harness implant 100 remains in position and the gastric tube 105 is removed (FIG. 8).

Figure 10:
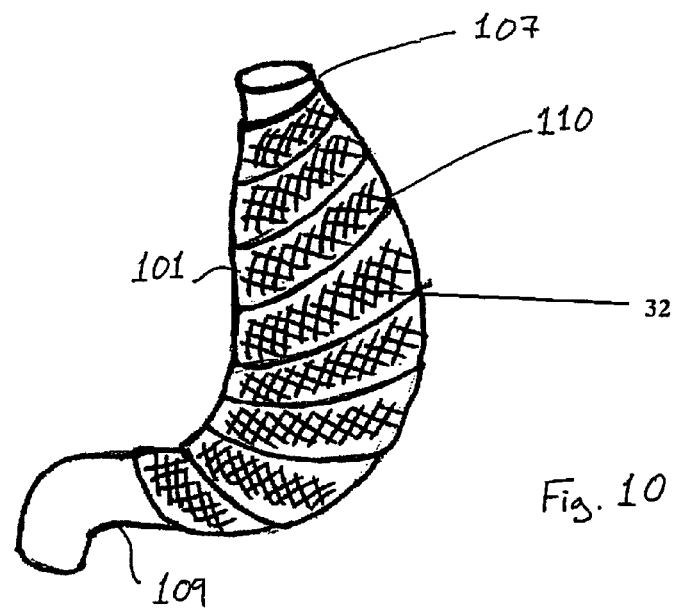
FIG. 10 is a perspective view of another gastric constriction device according to the invention in a strip configuration restricting the stomach.

In FIG. 10 there is illustrated another gastric constriction device 110 according to the invention, which is similar to the device 100 of FIG. 2, and similar elements in FIG. 10 are assigned the same reference numerals.

In this case the spiral band 101 extends around the stomach 24 in a spiral with each turn of the spiral partially overlapping an adjacent spiral turn.

FIG. 10 is a perspective view of a gastric harness implant 110 in a strip configuration 101 which in this case is wrapped around the stomach 24. The implant 110 may extend from the oesophagus 107 beyond the pylorus 109 to the small intestine. The strip configuration 101 may be passed around the stomach 24 and secured at the edges along attachment points 28 with sutures or staples.

Figure 11:
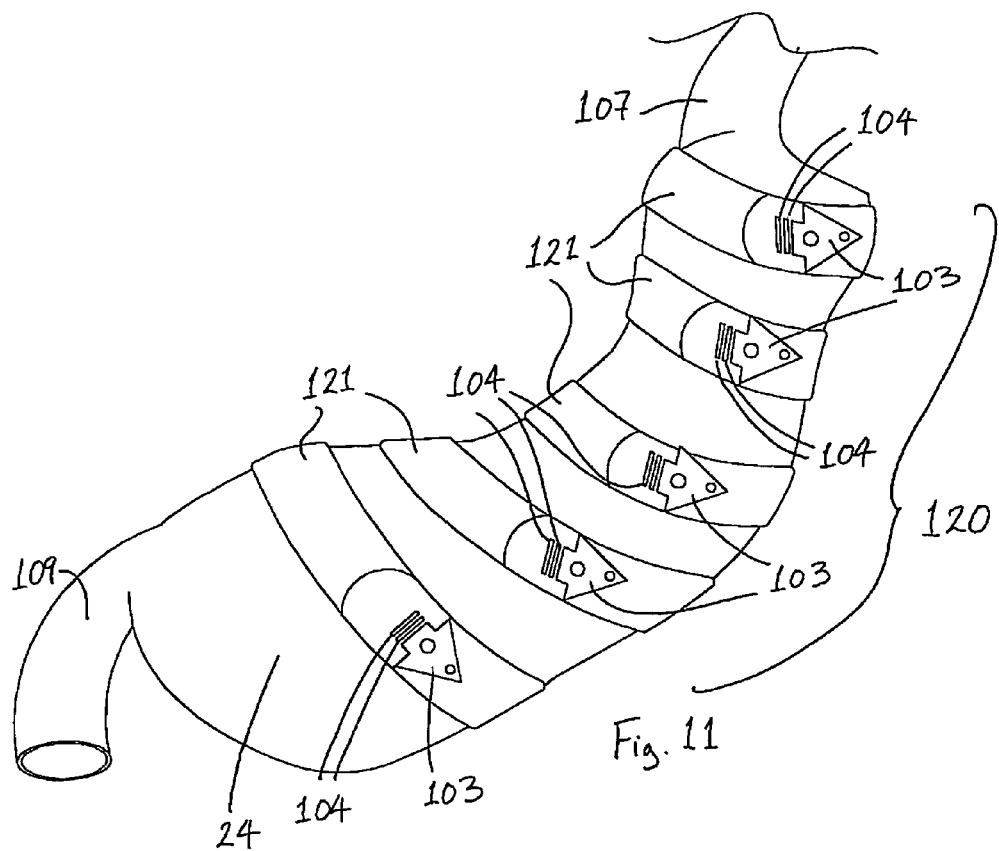
FIG. 11 is a perspective view of a further gastric constriction device according to the invention extending around a stomach.

FIGS. 11 to 13 illustrate another gastric constriction device 120 according to the invention, which is similar to the device 100 of FIG. 2, and similar elements in FIGS. 11 to 13 are assigned the same reference numerals.

In this case the device 120 comprises a plurality of loop bands 121. Each band 121 is suitable for being extended around the stomach 24 in a loop. By extending the plurality of loop bands 121 around the stomach 24 at a plurality of regions spaced along the stomach 24, the device 120 constricts the volume of the stomach 24, as illustrated in FIG. 11.

FIGS. 11 to 13 illustrate the gastric harness implant formed from individual bands. The gastric harness 120 can be formed from individual bands 121 or strips of material. Each individual band 121 has an attachment point for variable adjustment. The strips 121 can be placed from the oesophagus 107 to the pylorus 109. The gastric bands 121 provide a smooth interface with the stomach 24. The bands 121 are spaced such that the stomach 24 will not distend through the openings when food is ingested. The individual gastric bands 121 have preformed curves and variable adjustment means with spaced slits 104 to accommodate the taper point 103 (FIGS. 12 and 13).

Alternative fixing arrangements for fixing the loop bands 121 in position extending around the stomach 24 are illustrated in FIGS. 14 to 19.

The preformed individual bands 121 have two different attachment means. Each has a hole 300 for securement with a suture, staple, or other attachment means. A tool 122 is illustrated for moving the tapered point 103 through the slit 104 (FIGS. 14 to 16), and for moving the ratchet headpiece 123 through the corresponding slot 104.

Referring to FIGS. 20 and 21 there is illustrated another gastric constriction device 130 according to the invention, which is similar to the device 100 of FIG. 2, and similar elements in FIGS. 20 and 21 are assigned the same reference numerals.

In this case the device 130 comprises a continuous sheet 131 for extending over the entire wall of the stomach 24. In this manner, the sheet 131 may enclose the stomach 24 and thereby constrict the volume of the stomach 24.

FIG. 20 is a perspective view of a gastric harness implant 26 restricting the volume of the stomach 24. In another case the gastric harness implant 26 may extend from the oesophagus 107 beyond the pylorus 109 to the small intestine. The implant 26 may be of a film material such as those described below, for example the mesh 2E material.

In FIGS. 22 and 23, there is illustrated another suction device 140 according to the invention, which is similar to the suction device 105 of FIG. 4, and similar elements in FIGS. 22 and 23 are assigned the same reference numerals.

In this case the suction device 105 comprises a distal balloon member 142 and a proximal balloon member 141. In use, the balloon members 141, 142 are inflatable to engage the tissue wall to effect a seal prior to suction being applied.

Figure 25B:
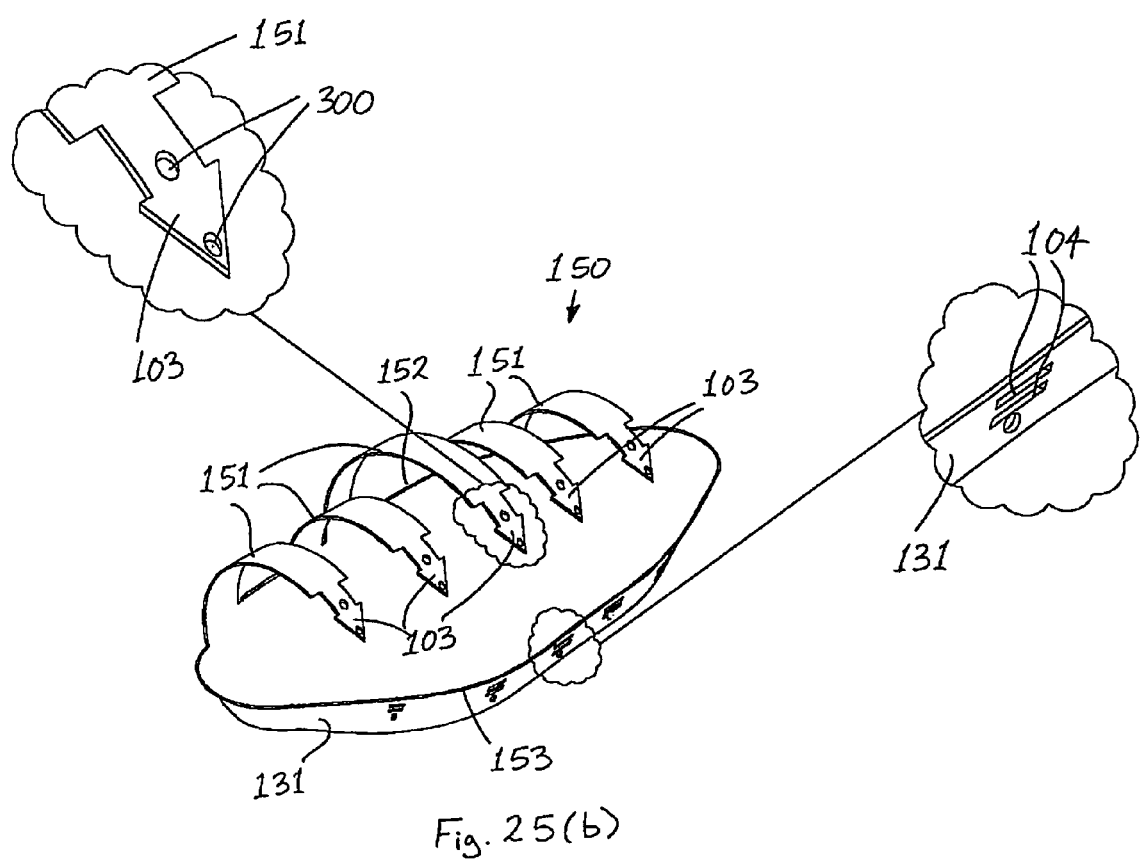

FIGS. 25 and 26 illustrate a further gastric constriction device 150 according to the invention, which is similar to the device 130 of FIGS. 20 and 21, and similar elements in FIGS. 25 and 26 are assigned the same reference numerals.

In this case, the sheet 131 is substantially shell-shaped, and extends over only part of the wall of the stomach 24. Five bands 151 extend from a first side 152 of the sheet 131 partially around the stomach 24 to a second side 153 of the sheet 131. In this manner, the bands 151 fix the sheet 131 in position extending over part of the wall of the stomach 24.

The bands 151 are releasably fixed to the second side 153 of the sheet 131 by means of the arrow-head member 103 and corresponding slots 104 arrangement.

FIGS. 25 and 26 illustrate the preformed gastric harness. The preformed gastric harness implant 150 is designed to engage the outer surface of the stomach 24 to reduce tension when food is ingested. The shape of the implant 150 can be adjusted such that the lesser and lower curvatures of the stomach 24 can be preferentially reduced to accommodate less volume when food is ingested. The three dimensional properties can facilitate sizing and placement. The implant 150 is curved to adjust to the shape of the stomach 24. Bands 151 are incorporated to wrap around the outer surface of the stomach 24. The spacing between bands 151 prevents stomach expansion when food is ingested. Slits 104 are placed in the implant 150 to accept the bands 151 with a tapered point 103, which permits instrument manipulation and placement. The tapered point 103 also has a hole 300 for accepting a suture, or staple for securing the implant 150. The implant 150 is positioned and the bands 151 are adjusted using the slits 104 in the implant 150 to adjust the tension.

Figure 27:
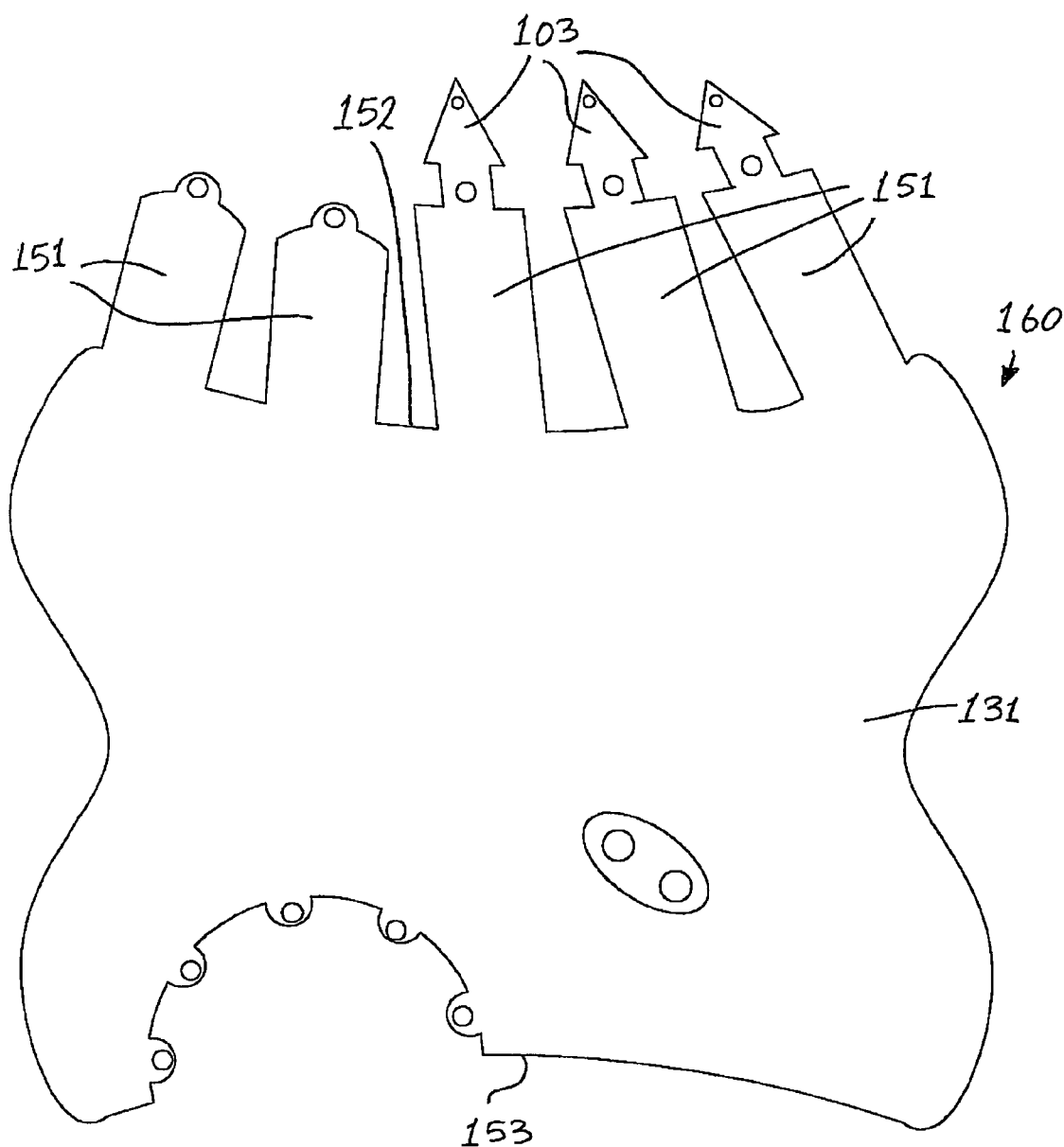
FIG. 27 is a plan view of another gastric constriction device according to the invention.
Figure 28:
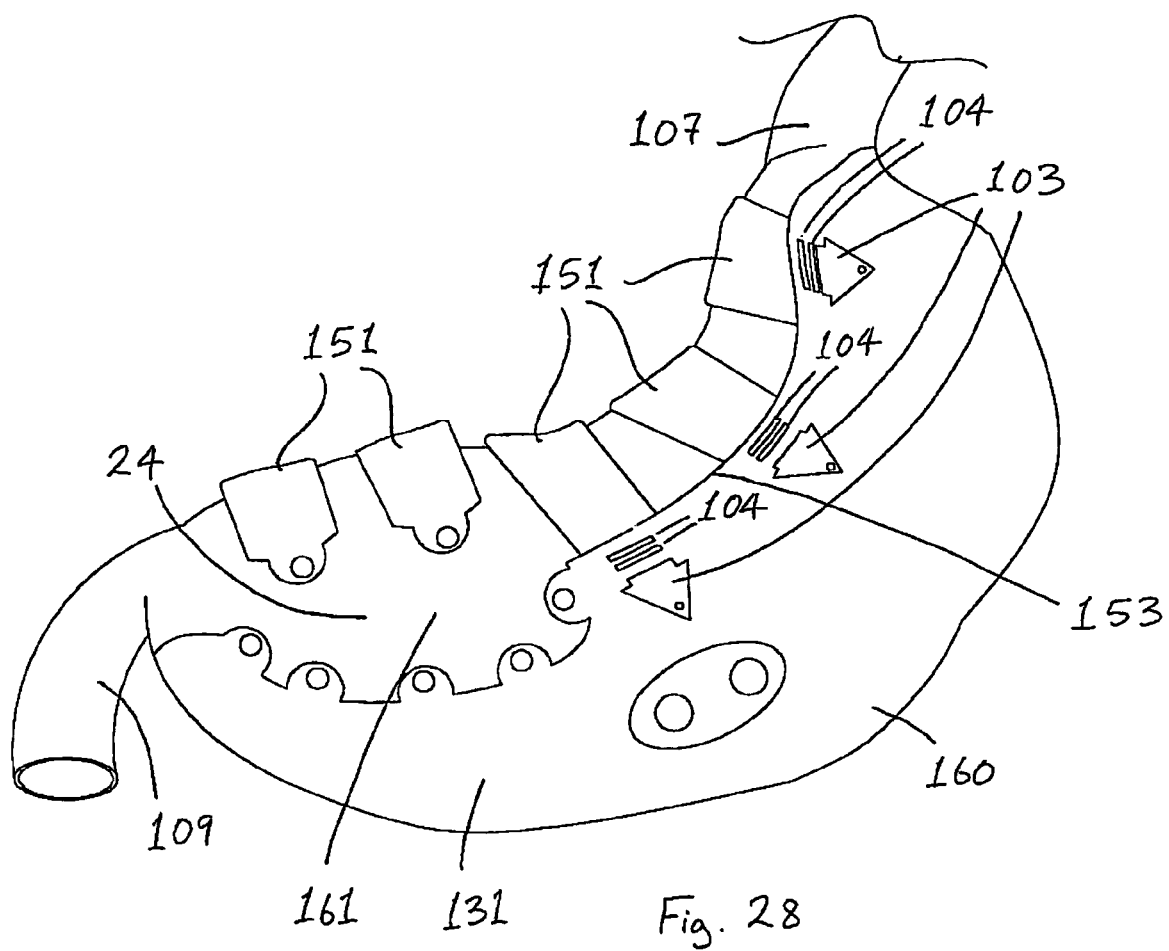
FIG. 28 is a perspective view of the device of FIG. 27 extending over the wall of a stomach.

In FIGS. 27 and 28, there is illustrated another gastric constriction device 160 according to the invention, which is similar to the device 150 of FIGS. 25 and 26, and similar elements in FIGS. 27 and 28 are assigned the same reference numerals.

In this case the lower two bands 151 extend from the first side 152 of the sheet 131 around the stomach 24 only partially towards the second side 153. These lower two bands 151 are not fixed to the second side 153. This arrangement results in an unconstricted portion of the stomach 161. In this manner, the device 160 restricts expansion of the majority of the stomach wall while facilitating expansion of this unconstricted portion 161.

The unconstricted portion 161 is therefore free to expand or bulge outwardly upon ingestion. This expansion may trigger the feeling of satiation due to the presence of the vagal nerves in this portion 161 of the stomach 24.

FIGS. 27 and 28 illustrate the gastric harness implant to modulate stomach expansion. A preformed implant 160 is designed such that areas of the stomach 24 can preferentially expand more under pressure when food is ingested. Placing the more elastic zones adjacent to the nerves that are responsible for signalling when stretch/tension receptors are activated may create the feeling of satiety. Preferential expansion is created in the area where more elastic zones are present or where the implant material is not present to constrain the stomach 24. Vagal nerves are more readily activated. An area for accepting a gastric pacing device may also be present. This may improve the efficacy of the concept.

Referring to FIG. 29 there is illustrated another gastric constriction device 170 according to the invention, which is similar to the device 130 of FIGS. 20 and 21, and similar elements in FIG. 29 are assigned the same reference numerals.

In this case, the sheet 131 extends around the full circumference of the stomach 24, but extends distally over only part of the wall of the stomach 24 from the oesophagus 107 approximately ⅓ to ⅔ of the distance towards the pylorus 109.

Figure 31:
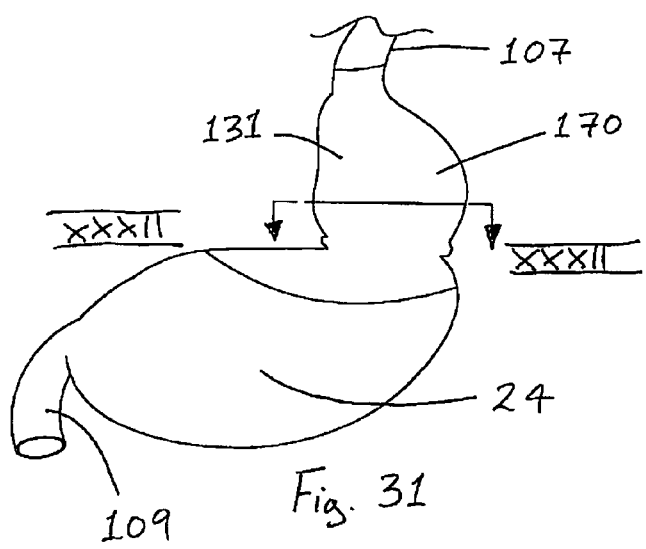
Figure 32:
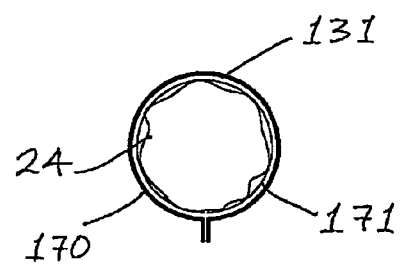
FIG. 32 is a view along line XXXII-XXXII in FIG. 31.

In use, a laparoscopic band 171 is extended around the stomach 24 (FIG. 30), and the device 170 is then extended around and along the stomach 24 with the band 171 located between the sheet 131 and the stomach wall (FIGS. 31 and 32).

To fix the sheet 131 in position extending over the wall of the stomach 24, a first region 172 of the sheet 131 is fixed directly to a second region 173 of the sheet 131.

FIGS. 29 to 32 illustrate the gastric harness implant used in conjunction with laparoscopic banding. The gastric harness 170 is used to prevent expansion of the fixed volume pouch created during laparoscopic banding. The gastric harness 170 conforms generally to the outside surface of the stomach 24 when the pouch is created. Holes 175 are present for accepting sutures and/or staples. The gastric harness 170 can be flared to minimise the risk of erosion and irritation. The cross section (FIG. 32) demonstrates the interface between the stomach pouch and gastric harness 170.

As illustrated in FIGS. 33 to 35, the laparoscopic band 171 may alternatively be extended around the sheet 131, after the sheet 131 has been extended around and along the stomach 24. In this case, the sheet 131 is located between the band 171 and the stomach wall.

The arrangement of FIGS. 29 to 32 is particularly advantageous. The technique used to insert the band 171 in FIGS. 29 to 32 is a simple, easy to practise technique. In particular, this technique would be compatible with many alternative banding devices.

FIGS. 33 and 34 are perspective views of a gastric harness implant 170 forming a gastric pouch 36. A gastric band 34 is provided. The band 34 may be a part of the implant 170 or separate from it. The gastric harness implant 170 in this configuration prevents the gastric pouch 36 from dilatation.

Figure 36:
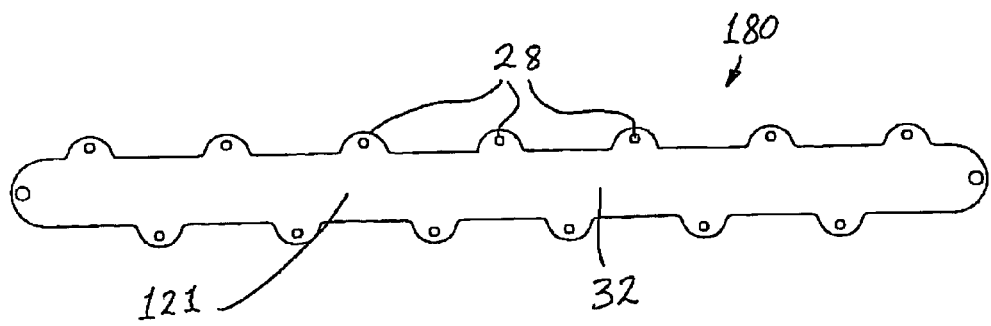
FIG. 36 is a plan view of another gastric constriction device according to the invention in a strip configuration with attachment points.
Figure 37:
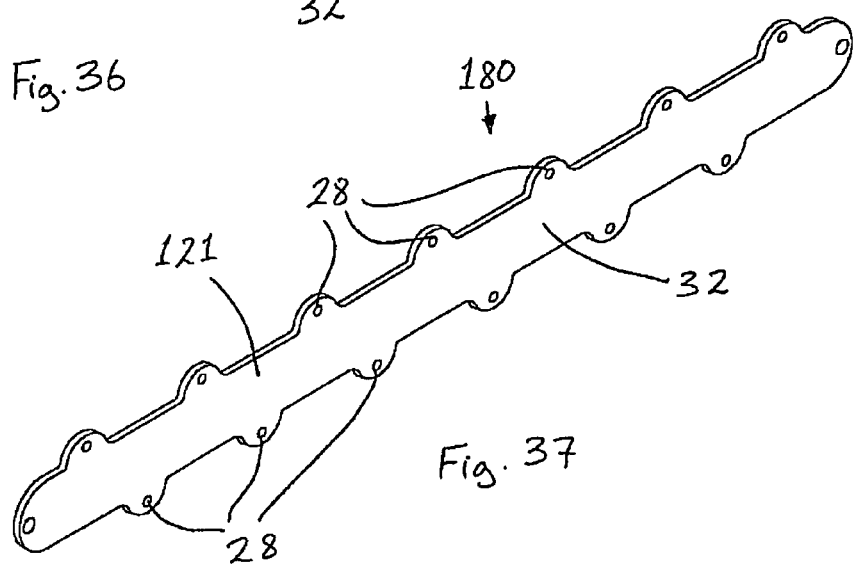
FIG. 37 is a perspective view of the device of FIG. 36.

In FIGS. 36 and 37 there is illustrated another gastric constriction device 180 according to the invention, which is similar to the device 120 of FIG. 11, and similar elements in FIGS. 36 and 37 are assigned the same reference numerals.

FIGS. 36 and 37 are perspective views of an implant material in a strip configuration 32 with attachment points 28.

FIGS. 36 and 37 illustrate the gastric harness strip with attachments. A strip 121 is disclosed for winding around the stomach 24. The strip 121 is intended to be placed laparoscopically using minimally invasive techniques and instrumentation. The strip 121 has attachment points 28 for accepting sutures, staples, or other securement means. The attachment points 28 are rounded and are in the form of eyelets to minimise the risk of tissue reaction and erosion. Cell openings are present for tissue in-growth and fixation to the stomach wall.

Figure 38:
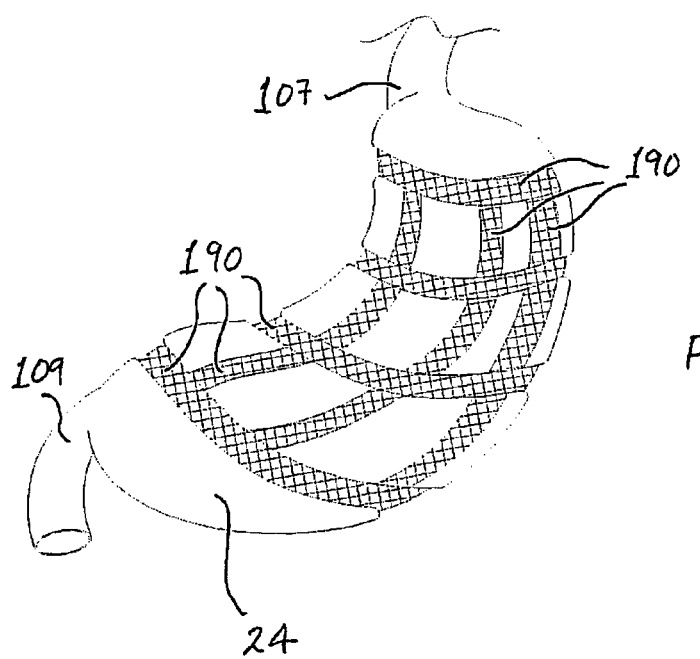
FIG. 38 is a perspective view of a further gastric constriction device according to the invention extending around a stomach.

In the embodiment of FIG. 38, a plurality of bands 190 are provided extending around the stomach 24 circumferentially and longitudinally along the stomach 24 for constricting the volume of the stomach 24.

Figure 39:
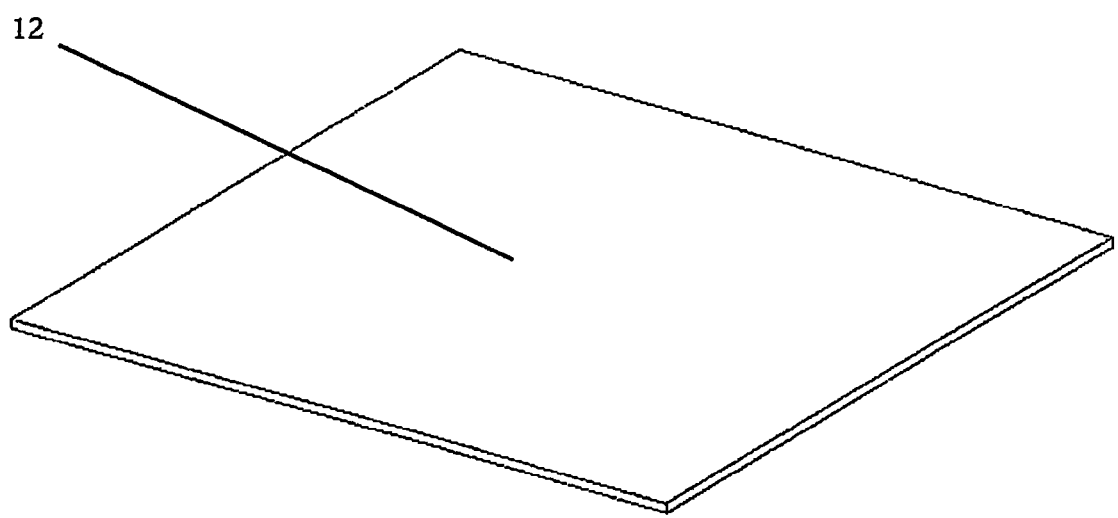
FIG. 39 is a perspective view of a material that can be machined to produce a gastric constriction device according to the invention.

FIG. 39 is a perspective view of a material that can be used to produce a gastric constriction device of the present invention. The material may be machined to produce a nonwoven gastric harness implant. The material illustrated in FIG. 39 is a perspective view of a nonwoven biocompatible film 12. The film 12 has known or discernible dimensions (width, length, and thickness), which can be modified or left intact in the manufacture of a gastric harness implant. In this case the film 12 is a single-layer, smooth-edged film.

Figure 40:
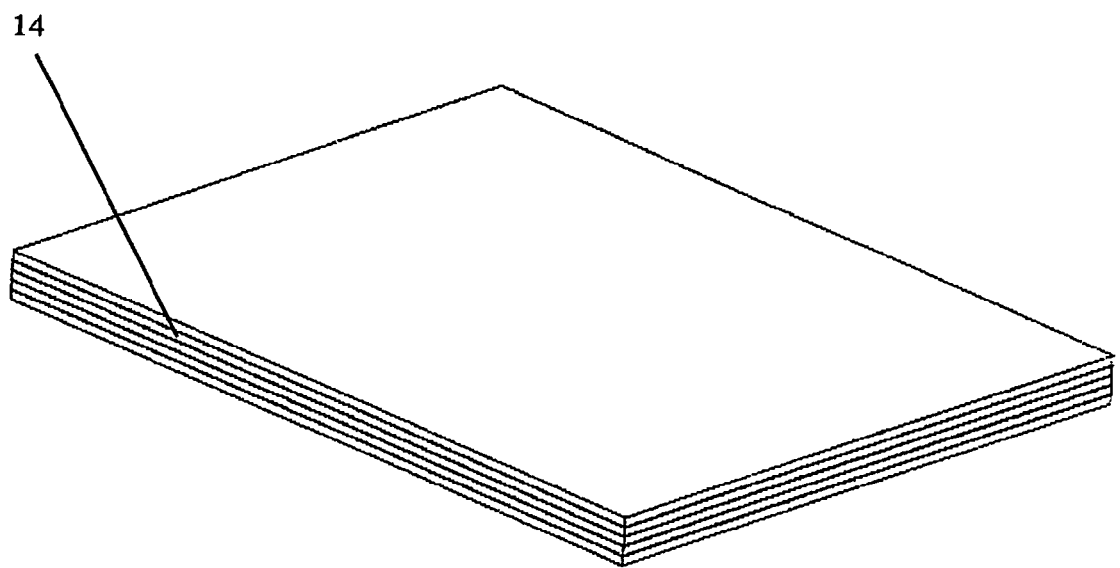
FIG. 40 is a perspective view of a laminated film structure showing layers of biocompatible films bonded together.

As shown in FIG. 40, the film 12 can be laminated to produce a film 14, which can also be used, with or without further modification, to manufacture the implants of the present invention. Multiple layers of biocompatible film 12 can be added together to improve the mechanical properties (e.g., tear resistance and burst strength) of the implant. For example, a first film 12 can be bonded to a second film 12. The bonding may be a thermal bond using hydraulic presses such as those manufactured by OEM Press Systems (Orange, Calif., USA).

Biocompatible materials useful in film 12 or film 14 can include non-absorbable polymers such as polypropylene, polyethylene, polyethylene terephthalate, polytetrafluoroethylene, polyaryletherketone, nylon, fluorinated ethylene propylene, polybutester, and silicone, or copolymers thereof (e.g., a copolymer of polypropylene and polyethylene); absorbable polymers such as polyglycolic acid (PGA), polylactic acid (PLA), polycaprolactone, and polyhydroxyalkanoate, or copolymers thereof (e.g., a copolymer of PGA and PLA); or tissue based materials (e.g., collagen or other biological material or tissue obtained from the patient who is to receive the implant or obtained from another person.) The polymers can be of the D-isoform, the L-isoform, or a mixture of both. An example of a biocompatible film 12 suitable for producing the laminated film structure 14 is expanded polytetrafluoroethylene.

In the case of a laminate 14, the various layers may be of the same or different materials. For example, in the case of an absorbable material, the material of the layers may be selected to have varying rates of absorption.

FIGS. 41 and 42 relate to an implant designated Mesh2E. Referring to, FIG. 41, a sinusoidal cell pattern 16 has been designed with radius 18. The properties of the cell pattern 16 are described in detail in FIG. 42.

Figure 43:
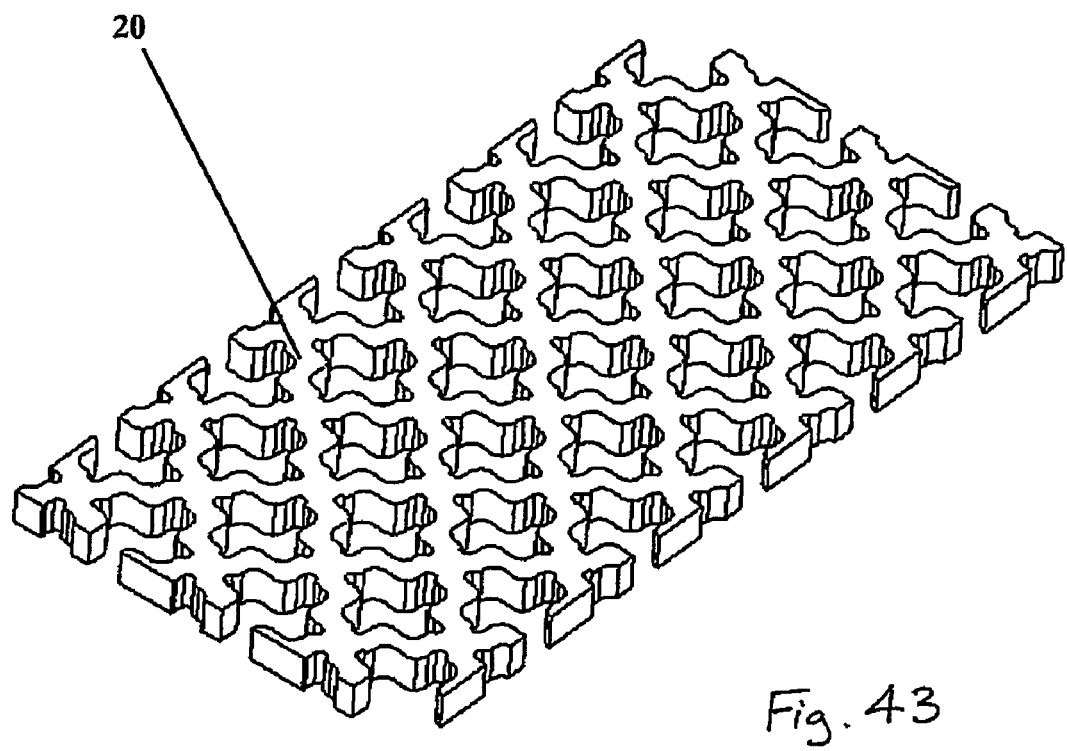
FIG. 43 is a diagram of an exemplary pore structure for Mesh2E.

FIG. 43 relates to a cell pattern structure 20 for cell pattern 16. The cell pattern structure 20 has been constructed using computer-aided design.

Figure 44:
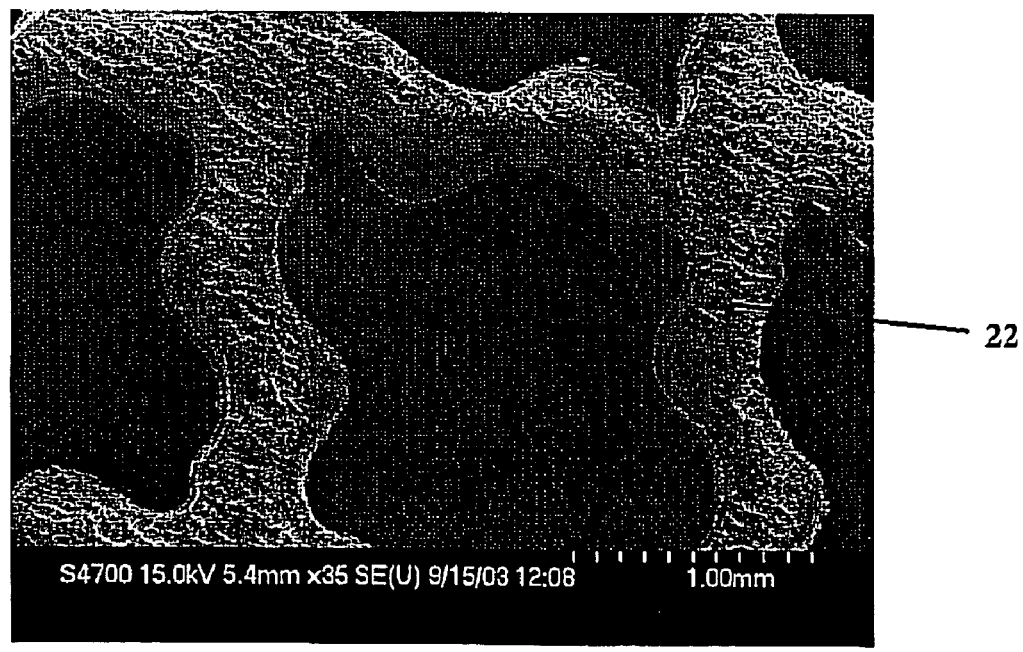
FIG. 44 is a micrograph of Mesh2E.

FIG. 44 is a micrograph of a machined film 22. The machined film 22 is in this case constructed using a die-punching tool machined to cell pattern structure 20. The machined film 22 has porosity, which can impart and support tissue ingrowth on high strength thin film substrates. A radius 18 may be applied to each cell pattern 16 corner to improve tear strength. Manufacturing methods to impart cell pattern 16 include, but are not limited to, laser machining, die punching, water jet cutting, and chemical etching. The lasers preferred for creating smooth edges on plastic films include, but are not limited to, $CO_2$, diode ultraviolet, or excimer lasers. An implant having cell pattern 16 is expected to confer benefit to a patient in which it is implanted because of the substantially smooth edges of cell pattern 16. Openings between 10 and 10,000 microns can be created in the film 22 with the geometry cell pattern 16. An opening of about 2000 microns creates an implant with adequate porosity for tissue ingrowth and good mechanical properties.

In FIGS. 45 to 51 there is illustrated a bio-absorbable material 200 suitable for use in forming the gastric constriction device of the invention. The bio-absorbable nature of the material 200 facilitates absorption of the device into the stomach wall over time.

As illustrated in FIG. 45, the material 200 has a laminate construction. Both the first layer 201 and the second layer 202 of the material 200 are porous to promote tissue in-growth. The first layer 201 has a higher pore density and smaller pore size than the second layer 202 (FIGS. 48 and 51). In this manner, the first layer 201 has a higher absorption rate and permits faster tissue remodelling than the second layer 202.

In use, the second layer 202 is located closer to the wall of the stomach 24 than the first layer 201.

FIGS. 45 to 51 illustrate the three-dimensional gastric harness scaffold. A scaffold 200 comprising layers 201, 202 of porous material is assembled. One layer 202 may have larger cells/pores with wider and/or thicker struts with longer degradation times. One layer may be composed of a material with a longer degradation time. The pores may be formed before the layers 201, 202 are attached to one another. The pores may have different dimensions and compositions, which vary the healing and degradation characteristics. Tissue will grow from the outside in and remodel at a controlled rate, which may permanently alter the volume potential of the stomach 24 due to the mechanical properties of the gastric wall after tissue has been deposited.

Referring to FIG. 52 there is illustrated another bio-absorbable material 210 suitable for use in forming the gastric constriction device of the invention.

In this case the material 210 comprises an anti-adhesion coating along at least part of the surface of the material 210.

In FIG. 53 there is illustrated a further bio-absorbable material 220 suitable for use in forming the gastric constriction device of the invention.

In this case the material 220 comprises an anti-adhesion filler 221 filling at least some of the pores.

FIGS. 52 and 53 illustrate the gastric harness with adhesion prevention material. The adhesion prevention material fills the cells and/or coats the porous material used to construct the gastric harness implant. The adhesion prevention material is absorbed at a controlled rate or stays on the material permanently to prevent unwanted adhesions between the gastric harness and internal organs.

Figure 54:
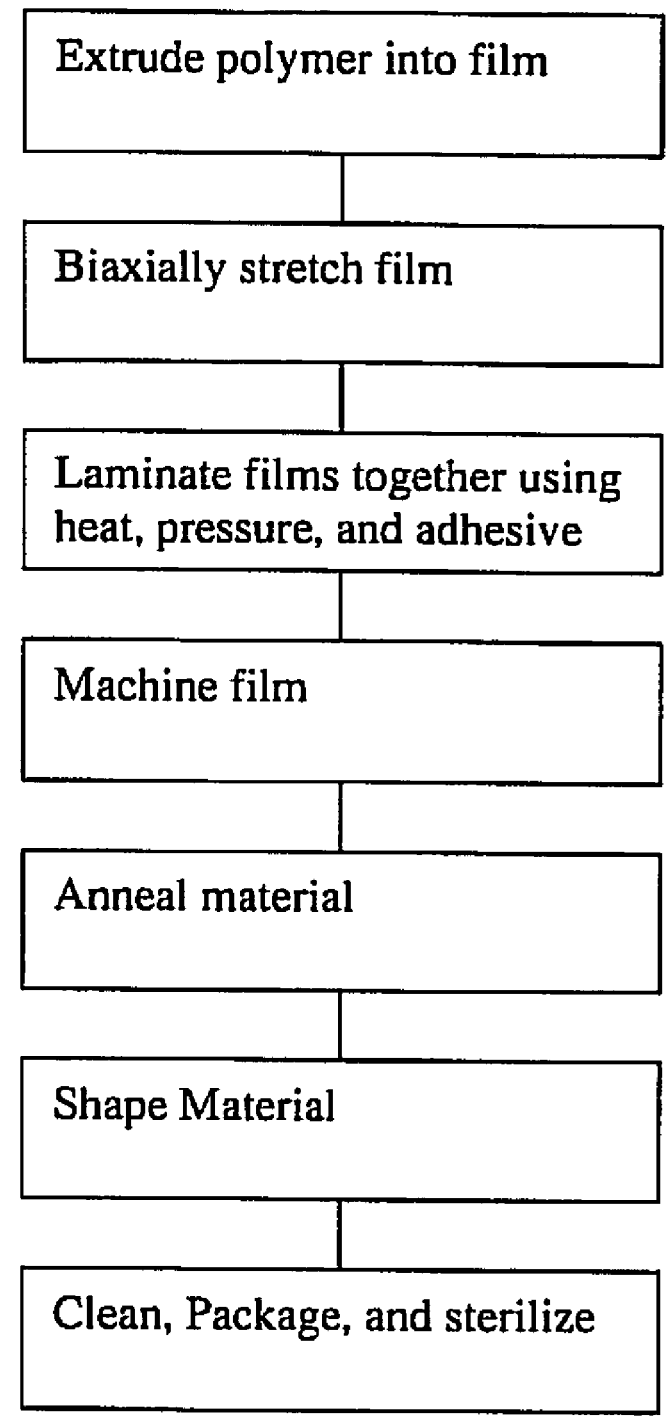
FIG. 54 is a flow chart illustrating some of the steps in a method of producing a gastric constriction device according to the invention.

FIG. 54 is a flow chart illustrating some of the steps in a method of producing a gastric harness implant of the invention.

In an alternative method, the steps of laminating the films together may be repeated after the step of machining the film.

The implant can have enhanced physical properties along its peripheral edges to improve suture or staple retention strength. The strength of material along the peripheral edges may be higher to improve the physical properties in this region so that sutures do not pull out and cause failure. The material content in these regions can be increased to improve the physical properties. In addition, attachment points can be created along the edge for receiving sutures, staples, or adhesives. The attachment points can be used to attach separate panels to one another to create the gastric implant.

Polytetrafluoroethylene (PTFE) polymer has useful properties as an implant material. PTFE can be processed into a microporous form using an expansion procedure. Bard Vascular Systems (Tempe, Ariz., USA) manufactures ePTFE. Expanded PTFE offers a combination of strength and flexibility together with extensive biocompatibility.

Medical implant applications for the soft tissue implant technology described above may include but are not limited to gastric banding and stomach restriction procedures. The soft tissue implant may be produced in a variety of shapes and sizes for the particular indication. One may select a non-absorbable gastric implant for morbidly obese patients that require permanent treatment and long-term durability and strength. Alternatively, one may select an absorbable soft tissue implant for patients that require temporary treatment of obesity when one wants to avoid the potential complications associated with a permanent implant.

In addition, the soft tissue implant product design may be produced in three-dimensional forms to facilitate sizing. An example is an implant with a curvature to construct a substantially cylindrical shape. A three dimensional structure could be machined using a system incorporating a third axis for micromachining. Alternatively, a substantially two-dimensional soft tissue implant could be thermoformed into a three-dimensional shape after machining.

EXAMPLES

Example 1

A nonwoven soft tissue implant was constructed using a biaxially oriented polymer film. Expanded PTFE film measuring 0.024 inches in thickness was obtained from Bard Vascular Systems (Tempe, Ariz., USA). Expanded PTFE was machined into the design Mesh2E cell patterns using a die punch produced by Elite Tool & Die (Smithstown, Ireland).

Example 2

A nonwoven soft tissue implant was constructed using biaxially oriented polymer films. Expanded PTFE film, part number 1TM22250, was obtained from BHA Technologies (Slater, Mo., USA). Twelve sheets of the film were placed between two sheets of DuPont Kapton 200HN film (Circleville, Ohio, USA). The sheet assembly was brought to 350° C. at 400 PSI of constant pressure for 15 minutes under vacuum. The laminated assembly was machined into the design Mesh2E cell patterns using a die punch produced by Elite Tool & Die (Smithstown, Ireland).

Example 3

A nonabsorbable gastric wrap was created using silicone tubing. A 100 cm length of tubing was perforated in 1 cm increments with a 2 mm punching tool. The gastric wrap was implanted into a canine at Charles River Laboratories (Ballina, Co. Mayo, Ireland). The assembly was used to wrap the stomach of a 22.8 kg canine. Interrupted Mersilk 1 sutures (Ethicon, Somerville, N.J., USA) were used to secure the gastric wrap in position against the stomach. In addition, a Maxon 1 monofilament absorbable suture (United States Surgical, Norwalk, Conn., USA) was used to support the wrap by running the suture through the wrap perforations along the longitudinal axis of the stomach. The canine was fed an unrestricted high calorie diet and sacrificed at 30 days. The weight of the animal at sacrifice was 21.6 kg. The gastric wrap had incorporated into the stomach wall with a moderate degree of adhesion formation and inflammation present.

A number of embodiments of the invention have been described. Nevertheless, it will be understood that various modifications may be made without departing from the spirit and scope of the invention.

The invention claimed is:

1. A method of constricting the volume of a stomach, the method comprising the steps of:
    sealing an entry to the stomach at the oesophagus, wherein the sealing is effected by inflating a sealing member;
    applying a suction to the interior of the stomach to at least partially collapse the stomach from a normal volume to a reduced volume;
    positioning a gastric constriction device relative to the stomach; and
    releasing the suction;
    wherein the gastric constriction device then applies a constricting force to the stomach to constrict the volume of the stomach.

2. The method of claim 1, wherein the method comprises a step of inserting a collapsing device at least partially into the interior of the stomach before sealing an entry to the stomach at the oesophagus.

3. The method of claim 1, wherein the method comprises a step of sealing an exit from the stomach at the pylorus before applying suction.

4. The method of claim 1, wherein the gastric constriction device is positioned extending at least partially around the stomach.

5. The method of claim 1, wherein the gastric constriction device is positioned extending at least partially around the stomach in a loop.

6. The method of claim 1, wherein the gastric constriction device is positioned extending at least partially around the stomach in a spiral.

7. The method of claim 1, wherein the gastric constriction device is positioned extending over at least part of the wall of the stomach.

8. The method of claim 1, wherein the gastric constriction device is positioned extending over only part of the wall of the stomach.

9. The method of claim 1, wherein the gastric constriction device is positioned extending over substantially the entire wall of the stomach to enclose the stomach.

10. The method of claim 1, wherein a first part of the gastric constriction device is positioned extending at least partially around the stomach, and a second part of the gastric constriction device is positioned extending over at least part of the wall of the stomach.

11. The method of claim 10, wherein the first part is positioned between the second part and the wall of the stomach.

12. The method of claim 1, wherein the method comprises the step of fixing the gastric constriction device in position relative to the stomach.

13. The method of claim 1, wherein the method comprises the step of adjusting the constricting force applied to the stomach.

14. The method of claim 1, wherein the gastric constriction device restricts expansion of a first region of the stomach wall and facilitates expansion of a second region of the stomach wall.

15. A method as claimed in claim 1 wherein the method comprises the step of stimulating gastric nerves.

* * * * *

UNITED STATES PATENT AND TRADEMARK OFFICE
CERTIFICATE OF CORRECTION

| | | |
|---|---|---|
| PATENT NO. | : 7,758,493 B2 | Page 1 of 1 |
| APPLICATION NO. | : 10/972044 | |
| DATED | : July 20, 2010 | |
| INVENTOR(S) | : Peter Gingras | |

It is certified that error appears in the above-identified patent and that said Letters Patent is hereby corrected as shown below:

Title page, column 2, line 12:
    Item (56); delete "Buchward" and insert -- Buchwald --, therefor.

Column 1, line 2:
    insert -- CROSS-REFERENCE TO RELATED APPLICATION -- under the title.

Signed and Sealed this

Fifth Day of October, 2010

David J. Kappos
*Director of the United States Patent and Trademark Office*